United States Patent [19]

Brooks et al.

[11] Patent Number: 5,516,789
[45] Date of Patent: May 14, 1996

[54] LIPOXYGENASE AND CYCLOOXYGENASE INHIBITING COMPOUNDS

[75] Inventors: Clint D. W. Brooks; Andrew O. Stewart, both of Libertyville; Anwer Basha, Lake Forest; Randy L. Bell, Lindenhurst, all of Ill.

[73] Assignee: Abbott Laboratories, Abbott Park, Ill.

[21] Appl. No.: 421,125

[22] Filed: Apr. 12, 1995

[51] Int. Cl.⁶ .................. A61K 31/405; C07D 209/14
[52] U.S. Cl. .................. 514/414; 514/224.8; 514/375; 514/406; 514/411; 514/416; 514/419; 514/427; 514/443; 514/445; 514/471; 514/595; 544/58.1; 548/224; 548/364.1; 548/375.1; 548/443; 548/445; 548/471; 548/472; 548/507; 548/526; 548/527; 548/561; 548/454; 564/56
[58] Field of Search ................ 548/454; 549/493, 549/58, 445; 564/56; 514/414, 443, 445, 471, 595

[56] References Cited

U.S. PATENT DOCUMENTS

| | | | |
|---|---|---|---|
| 3,637,795 | 1/1972 | Krenzer et al. | 260/463 |
| 3,742,008 | 6/1973 | Krenzer et al. | 260/455 |
| 3,840,564 | 10/1974 | Krenzer et al. | 260/347.3 |
| 3,948,967 | 4/1976 | Krenzer et al. | 260/463 |
| 4,873,259 | 10/1989 | Summers, Jr. et al. | 514/443 |
| 5,112,848 | 5/1992 | Brooks et al. | 514/424 |
| 5,185,363 | 2/1993 | Brooks et al. | 514/438 |
| 5,288,751 | 2/1994 | Brooks et al. | 514/438 |

Primary Examiner—Jacqueline Haley
Attorney, Agent, or Firm—Jerry F. Janssen

[57] ABSTRACT

Compounds having the structure

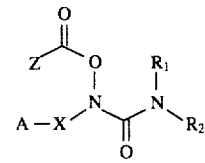

or a pharmaceutically acceptable salt thereof have activity as inhibitors of cylooxygenase and 5-lipoxygenase, reduce the biosynthesis of leukotrienes $B_4$, $C_4$, $D_4$, and $E_4$ and cylooxygenase products such as prostaglandins and thromboxane and are useful in the treatment of inflammatory and allergic disease states. The compounds have the structure indicated above wherein A is selected from (a) optinally substituted carbocyclic aryl, (b) optinally substituted furyl, (c) optinally substituted benzo[b]furyl, (d) optinally substituted thienyl, (e) optinally substituted pyridyloxy, (f) optinally substituted pyridylalkyl, (g) optinally substituted benzo[b]thienyl, (h) optinally substituted pyridyl, (i) optinally substituted quinolyl, and (j) optinally substituted indolyl; X is selected from (a) optionally substituted alkyl, (b) optionally substituted alkenyl, and (c) optionally substituted alkynyl; $R^1$ and $R^2$ are independently selected from hydrogen, hydroxy, and alkyl; and Z is a residue of a non-steroidal anti-inflammatory drug of the general formula Z—COOH.

8 Claims, No Drawings

LIPOXYGENASE AND CYCLOOXYGENASE INHIBITING COMPOUNDS

TECHNICAL FIELD

This invention relates to novel compounds possessing both lipoxygenase inhibitory activity and cycloxygenase inhibitory activity which are derived from the covalent bonding of a non-steroid anti-inflammatory drug (NSAID) through the carboxylic acid functionality to the oxygen atom of the N-hydroxy group of an N-hydroxyurea or hydroxamic acid 5-lipoxygenase (5-LO) inhibitor. The invention also relates to a pharmaceutical compositions containing these compounds and their use for inhibiting cyclooxygenase and liposygenase enzymes in humans and animals in need of such treatment, particularly for the treatment of inflammation.

BACKGROUND OF THE INVENTION

The use of so-called non-steroidal abtiinflammatory drugs ("NSAID's") for inhibiting cyclooxygenase is well known (see J. Lombardino in "Nonsteroidal Antiinflammatory Drugs", Wiley-Interscience, New York, 1985).

The enzyme 5-lipoxygenase catalyzes the first step leading to the biosynthesis of all the leukotrienes and therefore inhibition of this enzyme provides an approach to limit the effects of all the products of this pathway. Products of the 5-lipoxygenase cascade are extremely potent substances which produce a wide variety of biological effects, often in the nanomolar to picomolar concentration range (Sirois, P. Pharmacology of the Leukotrienes. Advances in Lipid Research. R. Paoletti, D. Kritchevesky, editors, Academic Press, 21: 79, 1985). Leukotrienes have been reported to be important mediators in several disease states including asthma, allergic rhinitis, rheumatoid arthritis, gout, psoriasis, adult respiratory disease syndrome, inflammatory bowel disease, endotoxin shock, ischemia-induced myocardial injury, central nervous pathophysiology, and atherosclerosis. Agents capable of abrogating the effects of these potent mediators of pathophysiological processes represent a promising class of therapeutic agents (Brooks, D. W., Bell, R. L., and Carter, G. W. Chapter 8. Pulmonary and Antiallergy Agents, *Annual Reports in Medicinal Chemistry*, Allen, R. C. ed., Academic Press 1988).

Formulations comprising a combination or mixture of non-steroidal antiinflammatory drugs (NSAID) and 5-lipoxygenase inhibitors have been described by Wellcome (WO 90/01929).

SUMMARY OF THE INVENTION

In its principal embodiment, the present invention provides novel compounds which comprise an NSAID, bonded through its carboxylic acid functionality to the oxygen atom of an N-hydroxyurea 5-lipoxygenase inhibitor to provide a dual-function pharmaceutical agent which inhibits both the cyclooxygenase enzyme and 5-lipoxygenase enzyme modulated metabolic pathways. The compounds of the present invention thus function as inhibitors of both cyclooxygenase and 5-lipoxygenase and reduce the biosynthesis of leukotrienes $B_4$, $C_4$, $D_4$, and $E_4$ and cyclooxygenase products such as prostaglandins and thromboxane and are useful in the treatment of inflammatory and allergic disease states.

In its principal embodiment, the present invention provides compounds of formula

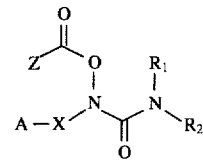

or a pharmaceutically acceptable salt thereof wherein A is selected from the group consisting of (a) carbocyclic aryl optionally substituted with (a-1) alkyl of one to six carbon atoms, (a-2) haloalkyl of one to six carbon atoms, (a-3) hydroxyalkyl of one to six carbon atoms, (a-4) alkoxy of one to twelve carbon atoms, (a-5) alkoxyalkoxyl in which the two alkoxy portions may each independently contain one to six carbon atoms, (a-6) alkylthio of one to six carbon atoms, (a-7) hydroxy, (a-8) halogen, (a-9) cyano, (a-10) amino, (a-11) alkylamino of one to six carbon atoms, (a-12) dialkylamino in which the two alkyl groups may independently contain one to six carbon atoms, (a-13) alkanoylamino of from two to eight carbon atoms, (a-14) N-alkanoyl-N-alkylamino in which the alkanoyl may contain two to eight carbon atoms and the alkyl groups may contain one to six carbon atoms, (a-15) alkylaminocarbonyl of two to eight carbon atoms, (a-16) dialkylaminocarbonyl in which the two alkyl groups may independently contain one to six carbon atoms, (a-17) carboxyl, (a-18) alkoxycarbonyl of two to eight carbon atoms, (a-19) phenyl, optionally substituted with alkyl of one to six carbon atoms, haloalkyl of one to six carbon atoms, alkoxy of one to six carbon atoms, hydroxy or halogen, (a-20) phenoxy, optionally substituted with alkyl of one to six carbon atoms, haloalkyl of one to six carbon atoms, alkoxy of one to six carbon atoms, hydroxy or halogen, (a-21) phenylthio, optionally substituted with alkyl of one to six carbon atoms, haloalkyl of one to six carbon atoms, alkoxy of one to six carbon atoms, hydroxy or halogen, (a-22) phenylalkyl wherein the alkyl portion is of one to twelve carbon atoms and the phenyl moiety is optionally substituted with alkyl of one to six carbon atoms, haloalkyl of one to six carbon atoms,alkoxy of one to six carbon atoms, hydroxy or halogen, (a-23) pyridyl, optionally substituted with alkyl of one to six carbon atoms, haloalkyl of one to six carbon atoms, alkoxy of one to six carbon atoms, hydroxy or halogen, (a-24) pyridyloxy, optionally substituted with alkyl of one to six carbon atoms, haloalkyl of one to six carbon atoms, alkoxy of one to six carbon atoms, hydroxy or halogen, (a- 25) pyridylalkyl wherein the alkyl portion is of one to twelve carbon atoms and the pryidyl portion is optionally substituted with alkyl of one to six carbon atoms, haloalkyl of one to six carbon atoms, alkoxy of one to six carbon atoms, hydroxy or halogen, (b) furyl, optionally substituted with (b-1) alkyl of one to six carbon atoms, (b-2) haloalkyl of one to six carbon atoms, (b-3) halogen, (b-4) phenyl, optionally substituted with alkyl of one to six carbon atoms, haloalkyl of one to six carbon atoms, alkoxy of one to six carbon atoms, hydroxy or halogen, (b-5) phenoxy, optionally substituted with alkyl of one to six carbon atoms, haloalkyl of one to six carbon atoms, alkoxy of one to six carbon atoms, hydroxy or halogen, (b-6) phenylthio, optionally substituted with alkyl of one to six carbon atoms, haloalkyl of one to six carbon atoms, alkoxy of one to six carbon atoms, hydroxy or halogen, (b- 7) phenylalkyl wherein the alkyl portion is of one to twelve carbon atoms and the phenyl moiety is optionally substituted with alkyl of one to six carbon atoms, haloalkyl of one to six carbon atoms, alkoxy of one to six carbon atoms, hydroxy or halogen, (b-8) pyridyl, optionally substituted with alkyl of one to six carbon atoms, haloalkyl of one to six carbon atoms, alkoxy of one to six carbon atoms, hydroxy or halogen, (b-9) pyridyloxy, optionally substituted with alkyl of one to six carbon atoms, haloalkyl of one to six carbon atoms, alkoxy of one to six carbon atoms, hydroxy or halogen, (b-10) pyridylalkyl wherein the alkyl portion is of one to twelve carbon atoms and the pryidyl portion is optionally substituted with alkyl of one to six carbon atoms, haloalkyl of one to six carbon atoms, alkoxy of one to six carbon atoms, hydroxy or halogen, (c) benzo[b]furyl substituted with (c-1) alkyl of one to six carbon atoms, (c-2) haloalkyl of one to six carbon atoms, (c-3) alkoxyl of one to six carbon atoms, (c-4) hydroxy, or (c-5) halogen, (d) thienyl, optionally substituted with (d-1) alkyl of one to six carbon atoms, (d-2) phenyl, optionally substituted with alkyl of one to six carbon atoms, haloalkyl of one to six carbon atoms, alkoxy of one to six carbon atoms, hydroxy or halogen, (d-3) phenoxy, optionally substituted with alkyl of one to six carbon atoms, haloalkyl of one to six carbon atoms, alkoxy of one to six carbon atoms, hydroxy or halogen, (d-4) phenylthio, optionally substituted with alkyl of one to six carbon atoms, haloalkyl of one to six carbon atoms, alkoxy of one to six carbon atoms, hydroxy or halogen, (d-5) phenylalkyl wherein the alkyl portion is of one to twelve carbon atoms and the phenyl moiety is optionally substituted with alkyl of one to six carbon atoms, haloalkyl of one to six carbon atoms, alkoxy of one to six carbon atoms, hydroxy or halogen, (d-6) pyridyl, optionally substituted with alkyl of one to six carbon atoms, haloalkyl of one to six carbon atoms, alkoxy of one to six carbon atoms, hydroxy or halogen, (e) pyridyloxy, optionally substituted with alkyl of one to six carbon atoms, haloalkyl of one to six carbon atoms, alkoxy of one to six carbon atoms, hydroxy or halogen, (f) pyridylalkyl wherein the alkyl portion is of one to twelve carbon atoms and the pryidyl portion is optionally substituted with alkyl of one to six carbon atoms, haloalkyl of one to six carbon atoms, alkoxy of one to six carbon atoms, hydroxy or halogen, (g) benzo[b]thienyl, optionally substituted with alkyl of one to six carbon atoms, haloalkyl of one to six carbon atoms, alkoxyl of one to six carbon atoms, hydroxy, or halogen, (h) pyridyl, optionally substituted with (h-1) alkyl of one to six carbon atoms, (h-2) haloalkyl of one to six carbon atoms, (h-3) alkoxyl of one to six carbon atoms, (h-4) hydroxy, (h-5) halogen, or (h-6) phenylalkyl wherein the alkyl portion is of one to twelve carbon atoms and the phenyl moiety is optionally substituted with alkyl of one to six carbon atoms, haloalkyl of one to six carbon atoms, alkoxy of one to six carbon atoms, hydroxy or halogen, (i) quinolyl, optionally substituted with alkyl of one to six carbon atoms, haloalkyl of one to six carbon atoms, alkoxyl of one to six carbon atoms, hydroxy, or halogen, and (j) indolyl, optionally substituted with alkyl of one to six carbon atoms, haloalkyl of one to six carbon atoms, alkoxyl of one to six carbon atoms, hydroxy, or halogen.

X is selected from the group consisting of (a) alkyl of one to six carbon atoms, optionally substituted with hydroxy, halogen, cyano, alkoxy of one to six carbon atoms, carboxy, alkoxycarbonyl of one to six carbon atoms, or aminocarbonyl, (b) alkenyl of two to six carbon atoms, optionally substituted with hydroxy, halogen, cyano, alkoxy of one to six carbon atoms, carboxy, alkoxycarbonyl of one to six carbon atoms, or aminocarbonyl, and (c) alkynyl of two to six carbon atoms, optionally substituted with hydroxy, halogen, cyano, alkoxy of one to six carbon atoms, carboxy, alkoxycarbonyl of one to six carbon atoms, or aminocarbonyl.

$R^1$ and $R^2$ are independently selected from the group consisting of hydrogen, hydroxy, and alkyl of one to six carbon atoms, provided that $R^1$ and $R^2$ are not both hydroxyl.

Z is a residue of a non-steroidal anti-inflammatory drug of the general formula Z—COOH selected from the group consisting of benoxaprofen, benzofenac, bucloxic acid, butibufen, carprofen, cicloprofen, cinmetacin, clidanac, clopirac, diclofenac, etodolac, fenbufen, fenclofenac, fenclorac, fenoprofen, fentiazac, flunoxaprofen, flurbiprofen, furaprofen, furobufen, furofenac, ibuprofen, ibufenac, indomethacin, indoprofen, isoxepac, ketoprofen, ketorolac, lonazolac, metiazinic acid, miroprofen, naproxen, oxaprozin, oxepinac, pirprofen, pirazolac, protizinic acid, sulindac, suprofen, tiaprofenic acid, tolmetin, zomepirac, 6-methoxynaphth-2-ylacetic acid (4-MNA), meclofenamic acid, and acetylsalicylic acid.

In another embodiment, the present invention provides pharmaceutical compositions which comprise a therapeutically effective amount of compound as defined above in combination with a pharmaceutically acceptable carrier.

In yet another embodiment, the present invention provides a method of treatment of a clinical condition for which an inhibitor of lipoxygenase or cyclooxygenase is indicated comprising administering to a mammal in need of such treatment a therapeutically effective amount of a compound as defined above.

DETAILED DESCRIPTION

As used throughout this specification and the appended claims, the following terms have the meanings specified.

The term "prodrug" as used herein refers to a non-steroidal antiinflammatory drug which is covalently bonded through its carboxy group to the hydroxy group of a N-hydroxyurea-derived lipoxygenase inhibitor. The prodrug is readily cleaved in vivo to release the biologically active parents. T. Higuchi and V. Stella provide a thorough discussion of the prodrug concept in "Pro-drugs as Novel Delivery Systems", Vol 14 of the A.C.S. Symposium Series, American Chemical Society (1975).

The term "alkyl" refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The term "alkylthio" refers to an alkyl group, as defined above, attached to the parent molecular moiety through a sulfur atom and includes such examples as methylthio, ethylthio, propylthio, n-, sec- and tert-butylthio and the like.

The terms "alkoxy" and "alkoxyl" denote an alkyl group, as defined above, attached to the parent molecular moiety through an oxygen atom. Representative alkoxy groups include methoxyl, ethoxyl, propoxyl, butoxyl, and the like.

The term "alkoxyalkyl" refers to an alkoxy group, as defined above, attached through an alkylene group to the parent molecular moiety.

The term "alkoxycarbonyl" represents an ester group; i.e. an alkoxy group, attached to the parent molecular moiety through a carbonyl group such as methoxycarbonyl, ethoxycarbonyl, and the like.

The term "alkenyl" denotes a monovalent group derived from a hydrocarbon containing at least one carbon-carbon double bond by the removal of a single hydrogen atom. Alkenyl groups include, for example, ethenyl, propenyl, butenyl, 1-methyl- 2-buten-1-yl and the like.

The term "alkyl" denotes a divalent group derived from a straight or branched chain saturated hydrocarbon by the removal of two hydrogen atoms, for example methylene, 1,2-ethylene, 1,1-ethylene, 1,3-propylene, 2,2-dimethylpropylene, and the like.

The term "alkenyl" denotes a divalent group derived from a straight or branched chain hydrocarbon containing at least one carbon-carbon double bond. Examples of alkenylene include —CH=CH—, —CH$_2$CH=CH—, —C(CH$_3$)=CH—, —CH$_2$CH=CHCH$_2$—, and the like.

The term "alkynyl" refers to a divalent group derived by the removal of two hydrogen atoms from a straight or branched chain acyclic hydrocarbon group containing a carbon-carbon triple bond. Examples of alkynylene include —CH[CH—, —CH[C—CH$_2$—, —CH[CH—CH(CH$_3$)— and the like.

The term "carbocyclic aryl" denotes a monovalent carbocyclic ring group derived by the removal of a single hydrogen atom from a monocyclic or bicyclic fused or non-fused ring system obeying the "4n+2 p electron" or Huckel aromaticity rule. Examples of carbocyclic aryl groups include phenyl, 1- and 2-naphthyl, biphenylyl and the like.

The term "(carbocyclic aryl)alkyl" refers to a carbocyclic ring group as defined above, attached to the parent molecular moiety through an alkylene group. Representative (carbocyclic aryl)alkyl groups include phenylmethyl or benzyl, phenylethyl, phenylpropyl, 1-naphthylmethyl, and the like.

The term "haloalkyl" denotes an alkyl group, as defined above, having one, two, or three halogen atoms attached thereto and is exemplified by such groups as chloromethyl, bromoethyl, trifluoromethyl, and the like.

The term "hydroxyalkyl" represents an alkyl group, as defined above, substituted by one to three hydroxyl groups with the proviso that no more than one hydroxy group may be attached to a single carbon atom of the alkyl group.

The term "phenoxy" refers to a phenyl group attached to the parent molecular moiety through an oxygen atom.

The term "phenylthio" refers to a phenyl group attached to the parent molecular moiety through a sulfur atom.

The term "pyridyloxy" refers to a pyridyl group attached to the parent molecular moiety through an oxygen atom.

By "pharmaceutically acceptable salt" it is meant those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M Berge, et al. describe pharmaceutically acceptable salts in detail in *J. Pharmaceutical Sciences*, 1977, 66: 1–19. The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetmethylammonium, methylmine, dimethylamine, as trimethylamine, triethylamine, ethylmine, and the like.

Asymmetric centers may exist in the compounds of the present invention. The present invention contemplates the various stereoisomers and mixtures thereof. Starting compounds of particular stereochemistry are either commercially available or are made by the methods detailed below and resolved by techniques well known in the organic chemical arts.

Examples of compounds contemplated as falling within the scope of the invention include:

N-[(S)-2-(6-methoxynaphth-2-yl)propionyloxy]-N-[1-(fur-3-yl)ethyl]urea,

N-[(S)-2-(6-methoxynaphth-2-yl)propionyloxy]-N-[1-(benzo[b]thien-2-yl)ethyl]urea, N-[2-(4-(2-methylpropyl)phenyl)propionyloxy]-N-[1-(benzo[b]thien-2-yl)ethyl]urea, N-[2-(N-(4-chlorobenzoyl)-5-methoxy-2-methyl-[1H]-indol-3-yl)acetoxy]-N-[1-(benzo[b]thien-2-yl)ethyl]urea, N-[2-(4-benzyloxy-3-chlorophenyl)acetyloxy]-N-[1-(benzo[b]thien-2-yl)ethyl]urea, N-[2-(4-(2-methylpropyl)phenyl)butyryloxy]-N-[1-(benzo[b]thien-2-yl)ethyl]urea, N-[2-(fluoren-2-yl)propionyloxy]-N-[1-(benzo[b]thien-2-yl)ethyl]urea, N-[2-(N-cinnamoyl-5-methoxy-2-methyl-[1H]-indol-3-yl)acetoxy]-N-[1-(benzo[b]thien-2-yl)ethyl]urea, N-[(5-chloro-6-phenylindan-2-yl)carbonyloxy]-N-[1-(benzo[b]thien-2-yl)ethyl]urea, N-[2-(2-(2,4-dichlorophenoxy)phenyl)acetyloxy]-N-[1-(benzo[b]thien-2-yl)ethyl]urea, N-[2-(3-phenoxyphenyl)propionyloxy]-N-[1-(benzo[b]thien-2-yl)ethyl]urea, N-[2-(3-phenylbenzo[b]fur-7-yl)propionyloxy]-N-[1-(benzo[b]thien-2-yl)ethyl]urea, N-[2-(2,3-dihydro-2-ethylbenzo[b]fur-5-yl)propionyloxy]-N-[1-(benzo[b]thien- 2-yl)ethyl]urea, N-[2-(4-(2-methylpropyl)phenyl)acetyloxy]-N-[1-(benzo[b]thien-2-yl)ethyl]urea, N-[2-(4-(2,3-dihydro-1-oxoisoindolyl)phenyl)propionyloxy]-N-[1-(benzo[b]thien-2-yl)ethyl] urea, N-[2-(5-fluoro-2-methyl-1((4-methylsuflinyl)phenyl)methylene)-(1H)indene-3-acetyloxy]-N-[ 1-(benzo[b]thien-2-yl)ethyl]urea, N-[(R)-2-(6-methoxynaphth-2-ylpropionyloxy]-N-[1-(4-phenylmethyloxyphenyl)ethyl]urea, N-[(S)-2-(6-methoxynaphth-2-yl)propionyloxy]-N-[3-(5-(4-fluorophenoxy)fur- 2-yl)-1-methyl-2-propynyl]urea, N-[2-(4-(2-methylpropyl)phenyl)propionyloxy]-N-[3-[5-(4-fluorophenylmethyl)fur- 2-yl]-1-methyl-2-propynyl]urea, N-[2-(4-(2-methylpropyl)phenyl)propionyloxy]-N-[1-(fur-3-yl)ethyl]urea, N-[(S)-2-(6-methoxynaphth-2-yl)propionyloxy]-N-[3-(5-(4-fluorophenylmethyl)thien- 2-yl)-(R)-1-methyl-2-propynyl]urea, N-[2-(4-benzyloxy-3-chlorophenyl)acetyloxy]-N-[3-(5-(4-fluorophenylmethyl)thien- 2-yl)-(R)-1-methyl-2-propynyl]urea, N-[2-(4-(2-methylpropyl)phenyl)butyryloxy]-N-[3-(5-(4-fluorophenylmethyl)thien- 2-yl)-(R)-1-methyl-2-propynyl]urea, N-[2-(fluoren-2-yl)propionyloxy]-N-[3-(5-(4-fluorophenylmethyl)thien-2-yl)-(R)-1-methyl- 2-propynyl]urea, N-[2-(N-cinnamoyl-5-methoxy-2-methyl-[1H]-indol-3-yl)acetoxy]-N-[3-(5-( 4-fluorophenylmethyl)thien-2-yl)-(R)-1-methyl-2-propynyl]urea, N-[(5-chloro-6-phenylindan-2-yl)carbonyloxy]-N-[3-(5-(4-fluorophenylmethyl)thien- 2-yl)-(R)-1-methyl-2-propynyl]urea, N-[2-(2-(2,4-dichlorophenoxy)phenyl)acetyloxy]-N-[3-(5-(4-fluorophenylmethyl)thien- 2-yl)-(R)-1-methyl-2-propynyl]urea, N-[2-(3-phenoxyphenyl)propionyloxy]-N-[3-(5-(4-fluorophenylmethyl)thien-2-yl)-1-methyl- 2-propynyl]urea, N-[2-(3-phenylbenzo[b]fur-7-yl)propionyloxy]-N-[3-(5-(4-fluorophenylmethyl)thien- 2-yl)-(R)-1-methyl-2-propynyl]urea, N-[2-(2,3-dihydro-2-ethylbenzo[b]fur-5-yl)propionyloxy]-N-[3-(5-( 4-fluorophenylmethyl)thien-2-yl)-(R)-1-methyl-2-propynyl]urea, N-[2-(4-(2-methylpropyl)phenyl)acetyloxy]-N-[3-(5-(4-fluorophenylmethyl)thien- 2-yl)-(R)-1-methyl-2-propynyl]urea, N-[2-(4-(2,3-dihydro-1-oxoisoindolyl)phenyl)propionyloxy]-N-[3-(5-( 4-fluorophenylmethyl)thien-2-yl)-(R)-1-methyl-2-propynyl]urea, N-[2-(5-fluoro-2-methyl-1((4-methylsufinyl)phenyl)methylene)-(1H)indene-3-acetyloxy]-N-[ 3-(5-(4-fluorophenylmethyl)thien-2-yl)-(R)-1-methyl-2-propynyl]urea, N-[2-(6-methoxynaphth-2-yl)acetyloxy]-N-[3-(5-(4-fluorophenylmethyl)thien- 2-yl)-(R)-1-methyl-2-propynyl]urea, N-[2-(6-methoxynaphth-2-yl)acetyloxy]-N-[1-(benzo[b]thien-2-yl)ethyl]urea, N-[(-2-acetoxybenzoyl)oxy]-N-[1-(benzo[b]thien-2-yl)ethyl]urea, N-[2-(acetoxybenzoyl)oxy]-N-[3-(5-(4-fluorophenoxy)fur-2-yl)-1-methyl- 2-propynyl]urea, N-[(S)-2-(6-methoxynaphth-2-yl)propionyloxy]-N-[1-(benzo[b]thien-2-yl)ethyl]-N'-methylurea, N-[(S)-2-(6-methoxynaphth-2-yl)propionyloxy]-N-[3-(5-(4-fluorophenylmethyl)thien- 2-yl)-(R)-1-methyl-2-propynyl]-N'-methylurea, N-[2-(2-(2,4-dichlorophenylamino)phenyl)acetyloxy]-N-[3-(5-(4-fluorophenylmethyl)thien- 2-yl)-(R)-1-methyl-2-propynyl]urea, N-[(2-(2,6-dichloro-3-methylphenylamino)benzoyl)oxy]-N-[3-(5-(4-fluorophenylmethyl)thien- 2-yl)-(R)-1-methyl-2-propynyl]urea, and N-[(2-(2,6-dichloro-3-methylphenylamino)benzoyl)oxy]-N-[1-(benzo[b]thien-2-yl)ethyl] urea.

Preferred compounds are those in which Z is a residue of a non-steroidal antiinflammatory drug of the general formula Z—COOH selected from the group consisting of benzofenac, bucloxic acid, butibufen, cicloprofen, cinmetacin, didanac, diclofenac, fenbufen, fenclofenac, fenoprofen, ibuprofen, ibufenac, indomethacin, ketoprofen, naproxen, sulindac, 6-methoxynaphth-2-ylacetic acid (4-MNA), acetylsalicylic acid, and meclofenamic acid.

Particularly preferred compounds include, but are not limited to:

N-[(S)-2-(6-methoxynaphth-2-yl)propionyloxy]-N-[1-(fur-3-yl)ethyl]urea,

N-[(S)-2-(6-methoxynaphth-2-yl)propionyloxy]-N-[1-(benzo[b]thien-2-yl)ethyl]urea, N-[2-(4-(2-methylpropyl)phenyl)propionyloxy]-N-[1-(benzo[b]thien-2-yl)ethyl]urea, N-[2-(N-(4-chlorobenzoyl)-5-methoxy-2-methyl-[1H]-indol-3-yl)acetoxy]-N-[ 1-(benzo[b]thien-2-yl)ethyl]urea, N-[(S)-2-(6-methoxynaphth-2-yl)propionyloxy]-N-[1-(4-phenylmethyloxyphenyl)ethyl]urea, N-[(S)-2-(6-methoxynaphth-2-yl)propionyloxy]-N-[3-(5-(4-fluorophenoxy)fur-2-yl)- 1-methyl-2-propynyl]urea N-[2-(4-(2-methylpropyl)phenyl)propionyloxy]-N-[3-(5-(4-fluorophenoxy)fur-2-yl)- 1-methyl-2-propynyl]urea, N-[2-(4-(2-methylpropyl)phenyl)propionyloxy]-N-[1-(fur-3-yl)ethyl]urea, N-[(S)-2-(6-methoxynaphth-2-yl)propionyloxy]-N-[3-(5-(4-fluorophenylmethyl)thien- 2-yl)-(R)-1-methyl-2-propynyl]urea, N-[2-(6-methoxynaphth-2-yl)acetyloxy]-N-[3-(5-(4-fluorophenylmethyl)thien- 2-yl)-(R)-1-methyl-2-propynyl] urea, N-[2-(6-methoxynaphth-2-yl)acetyloxy]-N-[1-(benzo[b]thien-2-yl)ethyl]urea, N-[(-2-acetoxybenzoyl)oxy]-N-[1-(benzo[b]thien-2-yl)ethyl]urea, and N-[2-(acetoxybenzoyl)oxy]-N-[3-(5-(4-fluorophenoxy)fur-2-yl)-1-methyl-2-propynyl]urea.

Lipoxygenase Inhibition Determination

Inhibition of leukotriene biosynthesis was evaluated in an assay, involving calcium ionophore-induced $LTB_4$ biosynthesis in human whole blood. Human heparinized whole blood was preincubated with test compounds or vehicle for 15 min at 37° C. followed by calcium ionophore A23187 challenge (final concentration of 50.0 µM) and the reaction terminated after 30 min by adding two volumes of methanol. The methanol extract was analyzed for $LTB_4$ using a commercially available immunoassay.

TABLE 1

In Vitro Inhibitory Potencies Against Stimulated $LTB_4$ Formation in Human Whole Blood

| Example | IC50 (µM) |
|---------|-----------|
| 1 | 4.0 |
| 3 | 5.8 |
| 4 | 1.8 |
| 18 | 1.3 |
| 19 | 1.2 |
| 20 | 9.9 |
| 37 | 0.16 |

Inhibition of Leukotriene and Prostaglandin Biosynthesis in vivo

Inhibition of the biosynthesis of leukotrienes in vivo after oral administration of compound was determined using a rat peritoneal anaphylaxis model similar to that described by Young and coworkers (Young, P. R.; Bell, R. L.; Lanai, C.; Summers, J. B.; Brooks, D. W.; Carter, G. W. (1991): Inhibition of leukotriene biosynthesis in the rat peritoneal cavity. Eur. J. Pharmacol 1991, 205, 259–266). In this model rats were injected intraperitoneally (ip) with rabbit antibody to bovine serum albumin (BSA) and three hours later injected ip with BSA to induce an antigen-antibody response. Rats were sacrificed 15 minutes after this challenge and the peritoneal fluids were collected and analyzed for leukotriene levels. Test compounds were administered by gavage one hour prior to the antigen challenge. To measure immunoreactive leukotriene levels in the various lavage fluids, the samples were diluted 1:3 (v/v) with the EIA buffer containing 100 mM phosphate, 1.5 mM sodium azide, 400 mM sodium chloride, 0.1 mM sodium EDTA and 0.1% BSA, pH 7.4. Methanol, at a final concentration of 22%, was included in the assay standards to compensate for the amount in the biological samples. EIA reagents for cysteinyl leukotrienes determination were purchased from, Cayman Chemical Co., Ann Arbor, Mich. The $LTE_4$ tracer was prepared in-house. The immunoassays for $LTE_4$ were then conducted as recommended by the manufacturer with the exception that volumes were adjusted to accommodate automation using a Cetus Propette (Cetus Corp., San Francisco, Calif.). The EIA was conducted in 96 well microtiter plates (Nunc Roskilde, Denmark) and optical density measured using a microplate reader (Vmax, Molecular Devices Corp., Menlo Park, Calif.). Percent inhibition values were determined by comparing the treatment group to the mean of the control group. Representative activity is shown in Table 2.

TABLE 2

| In Vivo Inhibitory Potencies of Compounds of this Invention | |
|---|---|
| Example | % Inhibition |
| 18 | 40% @ 15 mg/kg |
| 19 | 41% @ 15 mg/kg |
| 20 | 43% @ 15 mg/kg |

Inhibition of the biosynthesis of leukotrienes and prostaglandins in vivo was also demonstrated using a pleural inflammation model. Pleural inflammation was induced in male rats following the method of Rao et. al., Life Sci, 1993, 53, 52. Animals were dosed with experimental compounds in 0.2% HPMC one hour prior to the intrapleural injection of the calcium ionophore, A23187. The rats were lightly anesthetized with Penthrane (Abbott Laboratories) and injected intrapleurally with 0.5 ml of 2% ethanol in injectable saline (Abbott Laboratories) containing 20 µg of A23187 (Cal BioChem-Novabiochem). Thirty minutes later the animals were euthanized and the pleural cavities lavaged with ice cold saline. The lavage fluid was then added to ice cold methanol (final methanol concentration 30%) to lyse cells and precipitate protein.

The compounds of this invention inhibit the biosynthesis of prostaglandins in vivo. Cyclooxygenase activity of whole blood was determined by analysis of these samples for $TXB_2$ by EIA (Advanced Magnetics, Cambridge, Mass.). A representative compound is N-2-(6-methoxynaphth-2-yl)propionyloxy-N-3-[5-(4-fluorophenylmethyl)thien-2-yl]-1-methyl-2-propynylurea (Example 21) which exhibited 68% and 71% inhibition of the biosynthesis of prostaglandins and leukotrienes respectively at an oral dose of 10 mg/kg.

Inhibition of both leukotriene formation and prostaglandin formation was also shown in the dog. This was done using the method described by Carter et al. (Carter, G. W., Young, P. R., Albert, D. H., Bouska, J., Dyer, R., Bell, R. L., Summers, J. B. and Brooks, D. W.: J. Pharmacol. Exp. Ther. 256: 929–937, 1991.). Compound was suspended in 0.2% methylcellulose with a Potter-Elvehjem homogenizer equipped with a Teflon-coated pestle and administered orally to beagle dogs (Marshall Farms, North Rose, N.Y.) All animals were fasted overnight before dosing but allowed water ad libitum. Heparinized blood samples were obtained before and at various times after compound administration. Aliquots of blood were incubated at 37° with 50 µM with calcium ionophore, A23187. After 30 minutes, the blood was placed in an ice bath and analyzed for $LTB_4$ and $TXB_2$ as described above. An oral dose of 2 mg/kg of (R)-N-[2-(6-methoxynaphth-2-yl)propionyloxy]-(R)-N-[3-(5-(4-fluorophenylmethyl)thien-2-yl)-1-methyl-2-propynyl]urea (Example 21) gave 54% inhibition of $LTB_4$ and 47% inhibition of $TXB_2$ at 8 hours after dosing.

Pharmaceutical Compositions

The present invention also provides pharmaceutical compositions which comprise compounds of the present invention formulated together with one or more non-toxic pharmaceutically acceptable careers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginie acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

Synthesis of the Compounds

The preparation of the compounds of this invention is outlined in Scheme 1. The synthetic process involves a coupling between the hydroxyl group of an N-hydroxyurea or hydroxamic acid (5-lipoxygenase inhibitor) and the carboxylic add functionality of the non-steroidal anti-inflammatory drug (cyclooxygenase inhibitor) to obtain the novel antiinflammatory compounds having structure 1. The coupling reaction is performed using known methods of carboxylate activation such as 1,3-dicyclohexylcarbodiimide (DCC). In cases where the non-steroidal antiinflammatory drug (NSAID) contains functional groups which may interfere with the transformation outlined in Scheme 1, common methods of protection of these groups followed by deprotection at a later stage in the preparation of the desired product can be utilized. A general reference source for methods of protection and deprotection is T. W. Greene, "Protective Groups in Organic Synthesis", Wiley-Interscience, New York, 1981.

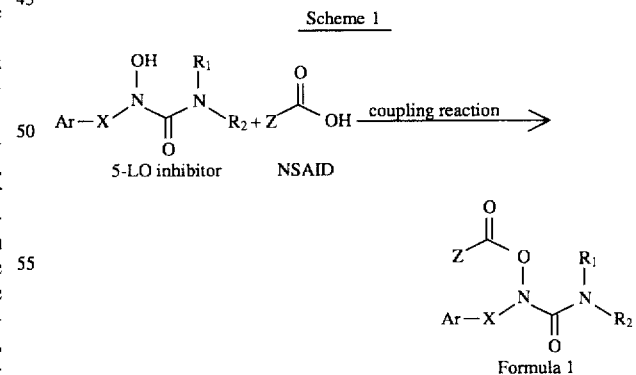

Compounds considered within the classification of non-steroidal antiinflammatory drugs (NSAIDS) have been documented by J. Lombardino in "Nonsteroidal Antiinflammatory Drugs", Wiley Interscience, New York (1985). Representative NSAIDS utilized in the present invention which are of the general form Z—COOH include, but are limited to, those listed in Table 2.

TABLE 2
Representative Non-Steroidal Antiinflammatory Drugs
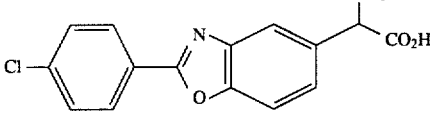
benoxaprophen
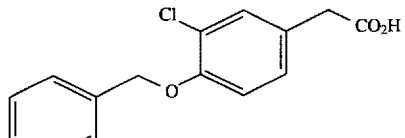
benzofenac
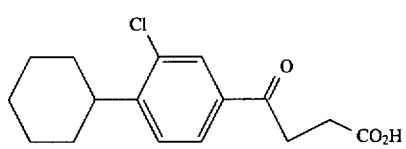
bucloxic acid
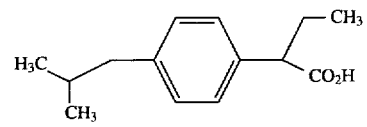
butibufen
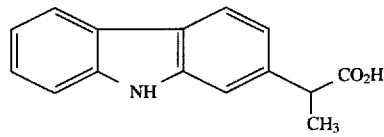
carprofen
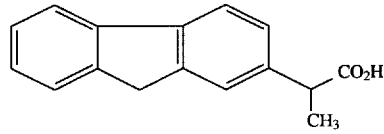
cicloprofen
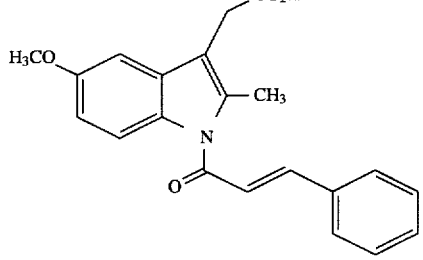
cinmetacin
TABLE 2-continued
Representative Non-Steroidal Antiinflammatory Drugs
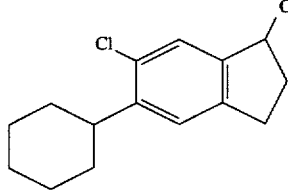
clidinac
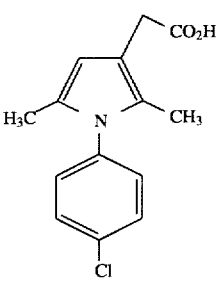
cloripac
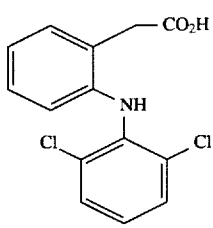
diclofenac
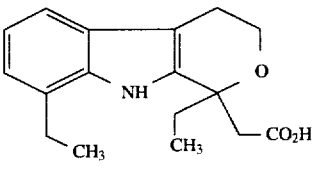
etodolac
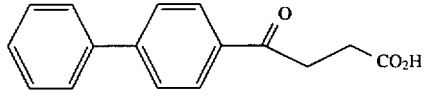
fenbufen
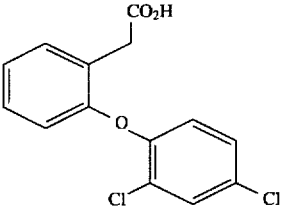
fenclofenac
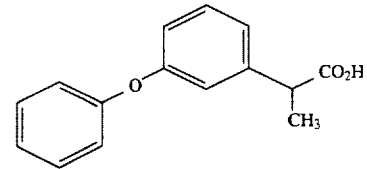
fenoprofen TABLE 2-continued
Representative Non-Steroidal Antiinflammatory Drugs
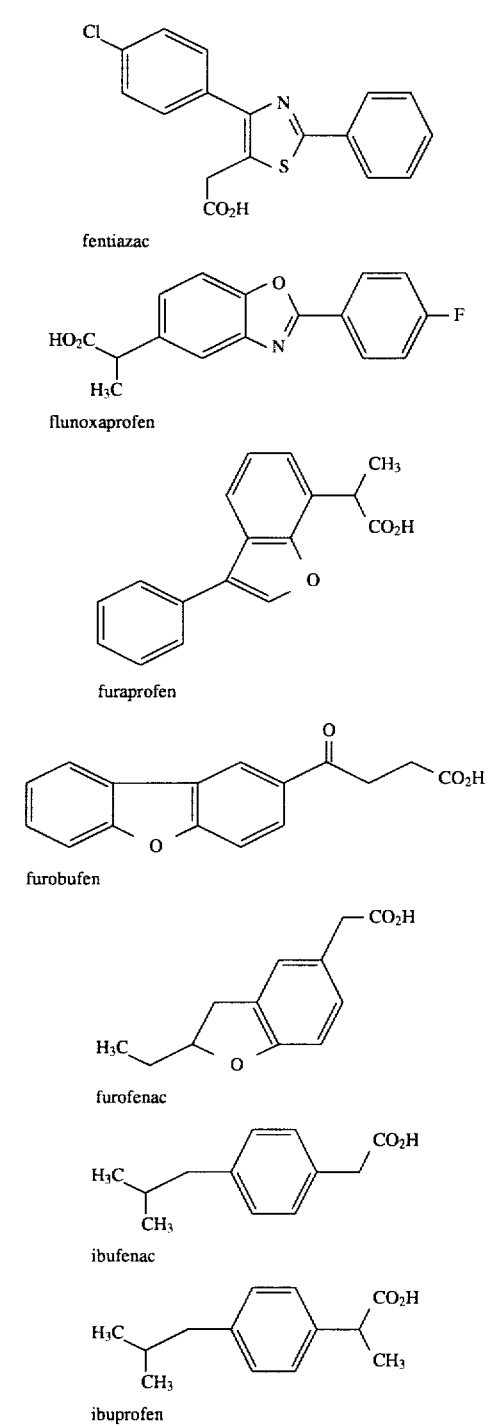
fentiazac
flunoxaprofen
furaprofen
furobufen
furofenac
ibufenac
ibuprofen
TABLE 2-continued
Representative Non-Steroidal Antiinflammatory Drugs
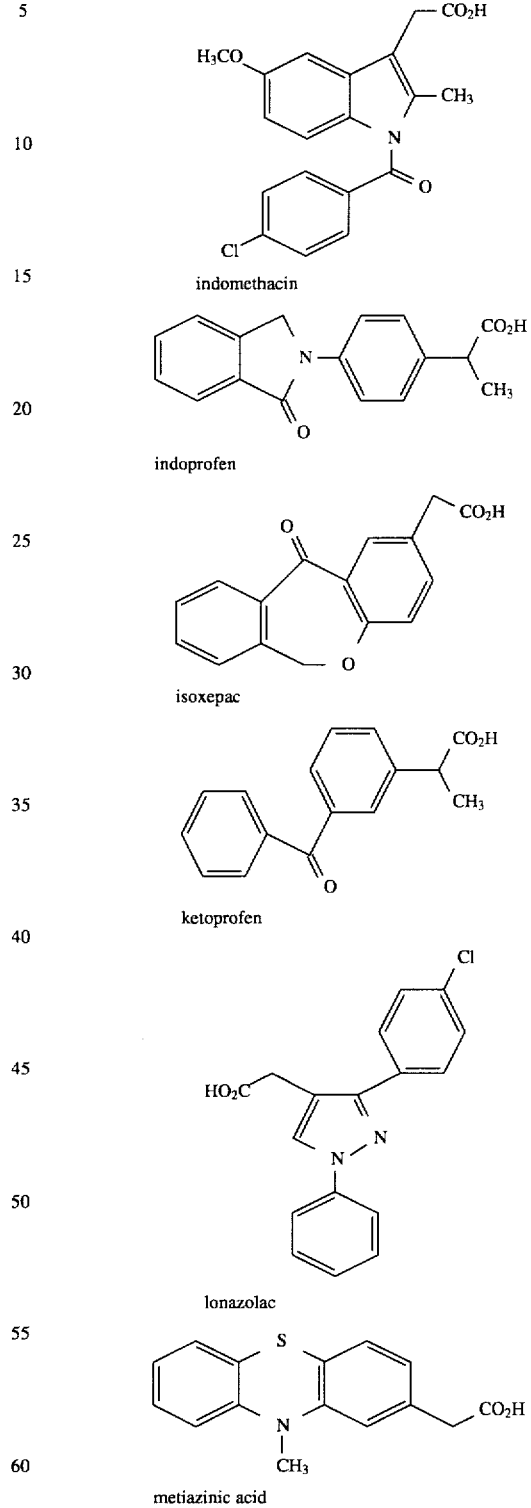
indomethacin
indoprofen
isoxepac
ketoprofen
lonazolac
metiazinic acid

TABLE 2-continued

Representative Non-Steroidal Antiinflammatory Drugs

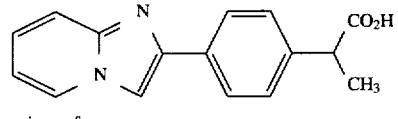
miroprofen

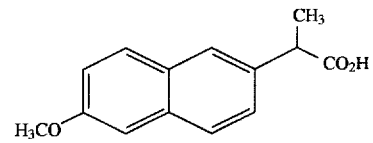
naproxen

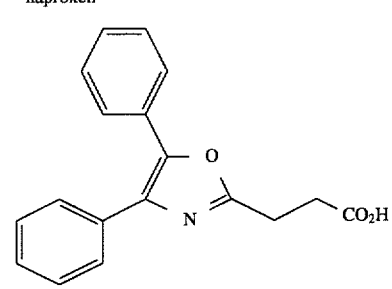
oxaprozin

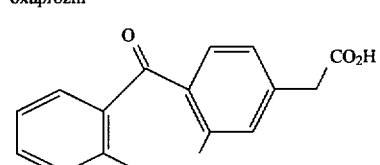
oxepinac

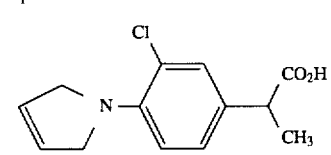
pirprofen

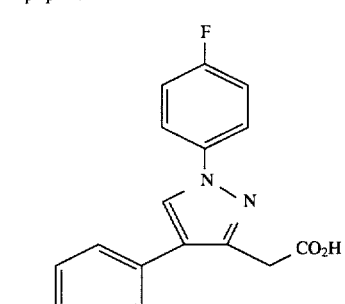
pirazolac

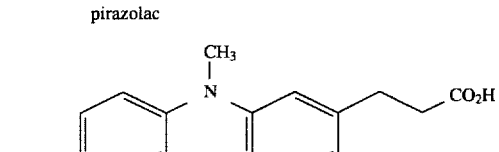
protozinic acid

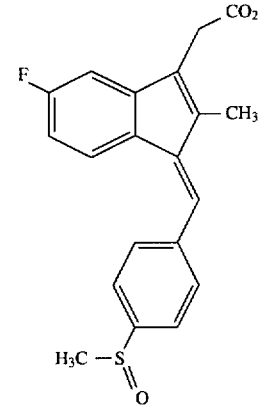
sulindac

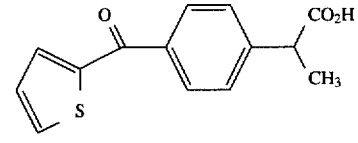
suprofen

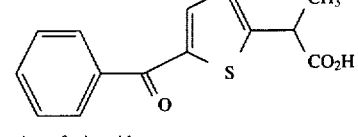
tiaprofenic acid

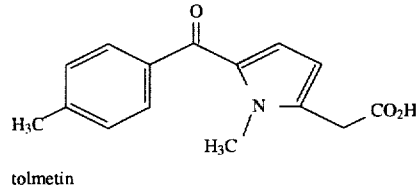
tolmetin

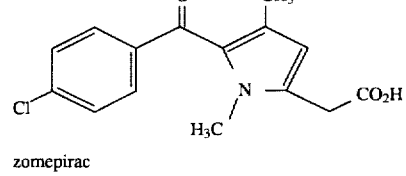
zomepirac

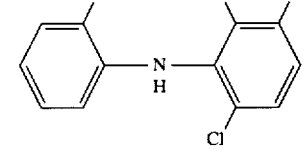
meclofenamic acid

The foregoing may be better understood by the following examples, which are presented for purposes of illustration and are not intended to limit the scope of the invention.

EXAMPLE 1

Preparation of
N-[(S)-2-(6-methoxynaphth-2-yl)propionyloxy]-
N-[1-(fur-3-yl)ethyl]urea

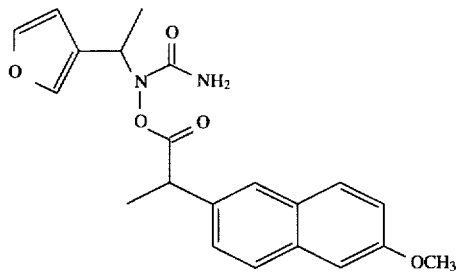

To a solution of N-1-(fur-3-yl)ethyl-N-hydroxyurea (1.00 g, 5.9 mmol), prepared as described in U.S. Pat. No. 5,112,848, in $CH_2Cl_2$ (25 mL) was added naproxen (1.35 g, 5.9 mmol) followed by dicyclohexylcarbodiimide (1.34 g, 6.49 mmol), and a crystal of 4-N,N-dimethylaminopyridine. The reaction was stirred for 18 hours. The reaction mixture was filtered through Celite and the filtrate was concentrated in vacuo. The residue was purified by chromatography on silica gel (ether), followed by crystallization in ethyl acetate/hexanes to give N-[(S)-2-(6-methoxynaphth- 2-yl)propionyloxy]-N-[1-(fur-3-yl)ethyl]urea (1.54 g). m.p. 128.5°– 134° C. $^1$H NMR (300 MHz, DMSO-$d_6$, mixture of diastereomers) δ 0.72 and 1.12 (bm, 3H), 1.48 (bm, 3H), 3.87 (s, 3H), 4.13 (bm, 1H), 5.14 (bm, 1H), 6.79 and 6.94 (bs, 2H), 7.16 (m, 2H), 7.29–7.46 (m, 3H), 7.69–7.86 (m, 3H). MS (DCI/$NH_3$) m/e 383 (M+H)$^+$. Analysis calc'd for $C_{21}H_{22}N_2O_5$: C, 65.95; H, 5.80; N, 7.33. Found: C, 65.39; H, 5.80; N, 7.26.

EXAMPLE 2

Preparation of
N-[(S)-2-(6-methoxynaphth-2-yl)propionyloxy]-N
-[1-(benzo[b]thien- 2-yl)ethyl]urea

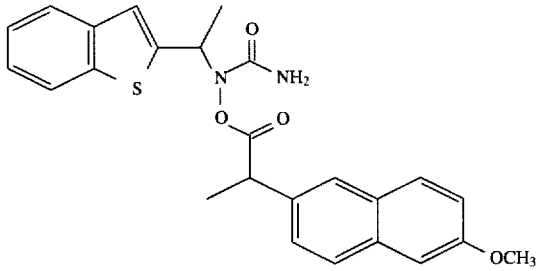

The desired material was prepared according to the procedure of Example 1 substituting N-1-(benzo[b]thien-2-yl)ethyl-N-hydroxyurea, prepared as described in U.S. Pat. No. 4,873,259, for N-1-(fur-3-yl)ethyl-N-hydroxyurea. m.p. 62°–70° C. $^1$H NMR (500 MHz, DMSO-$d_6$, mixture of diastereomers) δ 0.99 and 1.36 and 1.51 (bm, 6H), 3.88 and 3.90 (s, 3H), 4.16 (bm, 1H), 5.55 (q, 1H, J=6.5 Hz), 6.85 (bs, 2H), 7.10–7.89 (bm, 11H). MS (DCI/$NH_3$) m/e 449 (M+H)$^+$.

EXAMPLE 3

Preparation of
N-[2-(4-(2-methylpropyl)phenyl)propionyloxy]-N
-[1-(benzo[b]thien- 2-yl)ethyl]urea

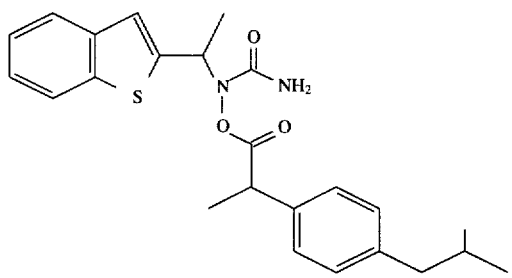

The desired material was prepared according to the procedure of Example 2, except substituting ibuprofen for naproxen. m.p. 123°–128° C. $^1$H NMR (300 MHz, DMSO-$d_6$, mixture of diastereomers) δ 0.85 (m, 6H), 0.97 and 1.34 and 1.41 (bm, 6H), 1.73–1.93 (m, 1H), 2.37 and 2.48 (bd, 2H, J=6.5 Hz), 3.94 (q, 1H, J= 6.5 Hz), 5.56 (q, 1H, J=6.5 Hz), 6.66 and 6.87 (bs, 2H), 7.20 (bs, 3H), 7.28–7.40 (m, 2H), 7.71 (m, 1H), 7.85 (m, 1H). MS (DCI/$NH_3$) m/e 425 (M+H)$^+$. Analysis calc'd for $C_{24}H_{28}N_2O_3S$: C, 67.89; H, 6.65; N, 6.60. Found: C, 68.00; H, 6.94; N, 6.81.

EXAMPLE 4

Preparation of
N-[2-(N-(4-chlorobenzoyl)-5-methoxy-2-
methyl-[1H]-indol-3-yl)acetoxy]-N-[
1-(benzo[b]thien-2-yl)ethyl]urea

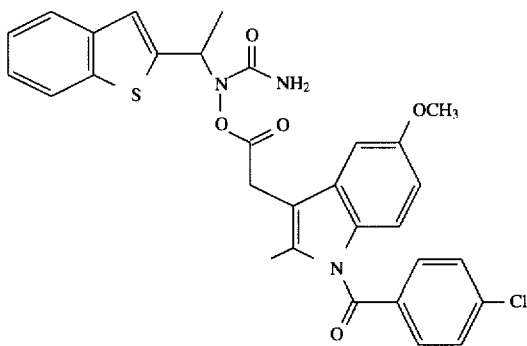

The desired material was prepared according to the procedure of Example 2, except substituting indomethacin for naproxen. m.p. 153°–155° C. $^1$H NMR (300 MHz, DMSO-$d_6$, mixture of diastereomers) δ 1.32 (bd, 3H, J=6 Hz), 2.09 (bs, 3H), 3.71 (s, 3H), 3.96 (bm, 2H), 5.62 (bm, 1H), 6.74 (dd, 1H, J=2, 9.5 Hz), 6.91–7.04 (m, 4H), 7.09 (m, 1H), 7.29 (m, 2H), 7.61 (m, 5H), 7.79 (m, 1H). MS (DCI/$NH_3$) m/e 576 (M+H)$^+$. Analysis calc'd for $C_{30}H_{26}ClN_3O_5S$: C, 62.55; H, 4.55; N, 7.29. Found: C, 62.64; H, 4.64; N, 7.27.

EXAMPLE 5

Preparation of
N-[2-(4-benzyloxy-3-chlorophenyl)acetyloxy]-
N-[1-(benzo[b]thien-2-yl)ethyl]urea The desired compound is prepared according to the method of Example 2, except substituting butibufen for naproxen.

EXAMPLE 6

Preparation of
N-[2-(4-(2-methylpropyl)phenyl)butyryloxy]-
N-[1-(benzo[b]thien-2-yl)ethyl]urea.

The desired compound is prepared according to the method of Example 2, except substituting benzofenac for naproxen.

EXAMPLE 7

Preparation of
N-[2-(fluoren-2-yl)propionyloxy]-N-[1-
(benzo[b]thien-2-yl)ethyl]urea The desired compound is prepared according to the method of Example 2, except substituting cycloprofen for naproxen.

EXAMPLE 8

Preparation of
N-[2-(N-cinnamoyl-5-methoxy-2-methyl-[1H]-
indol-3-yl)acetoxy]-N-[
1-(benzo[b]thien-2-yl)ethyl]urea The desired compound is prepared according to the method of Example 2, except substituting cinmetacin for naproxen.

EXAMPLE 9

Preparation of
N-[(5-chloro-6-phenylindan-2-yl)carbonyloxy]-
N-[1-(benzo[b]thien- 2-yl)ethyl]urea The desired compound is prepared according to the method of Example 2, except substituting clidinac for naproxen.

EXAMPLE 10

Preparation of
N-[2-(2-(2,4-dichlorophenoxy)phenyl)acetyloxy]-
N-[1-(benzo[b]thien- 2-yl)ethyl]urea The desired compound is prepared according to the method of Example 2, except substituting fenclofenac for naproxen.

EXAMPLE 11

Preparation of
N-[2-(3-phenoxyphenyl)propionyloxy]-N-
[1-(benzo[b]thien-2-yl)ethyl]urea The desired compound is prepared according to the method of Example 2, except substituting fenoprofen for naproxen.

EXAMPLE 12

Preparation of
N-[2-(3-phenylbenzo[b]fur-7-yl)propionyloxy]-
N-[1-(benzo[b]thien- 2-yl)ethyl]urea The desired compound is prepared according to the method of Example 2, except substituting furaprofen for naproxen.

EXAMPLE 13

Preparation of
N-[2-(2,3-dihydro-2-ethylbenzo]b]fur-5-yl)
propionyloxy]-N-[1-(benzo[ b]thien-2-yl)ethyl]urea The desired compound is prepared according to the method of Example 2, except substituting furofenac for naproxen.

EXAMPLE 14

Preparation of
N-[2-(4-2-methylpropyl)phenyl)acetyloxy]-N-
[1-(benzo[b]thien-2-yl)ethyl]urea The desired compound is prepared according to the method of Example 2, except substituting ibufenac for naproxen.

EXAMPLE 15

Preparation of
N-[2-(4-(2,3-dihydro-1-oxoisoindolyl)phenyl)
propionyloxy]-N-[1-(benzo[ b]thien-2-yl)ethyl]urea The desired compound is prepared according to the method of Example 2, except substituting indoprofen for naproxen.

EXAMPLE 16

Preparation of
N-[2-(5-fluoro-2-methyl-1((4-methylsuflinyl)
phenyl)methylene)-( 1H)indene-3-acetyloxy]-N-[1-
(benzo[b]thien-2-yl)ethyl]urea The desired compound is prepared according to the method of Example 2, except substituting sulindac for naproxen.

EXAMPLE 17

Preparation of N-[(R)-2-(6-methoxynaphth-2-
ylpropionyloxy)]-N-[1-(
4-phenylmethyloxyphenyl)ethyl]urea

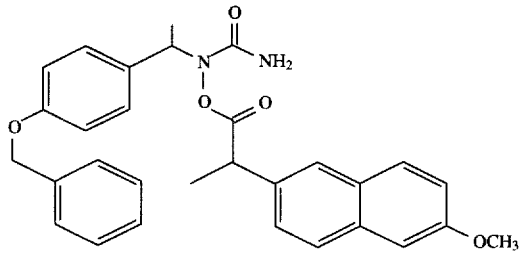

The desired material was prepared according to the procedure of Example 1 substituting N-(1-(4-phenylmethyloxyphenyl)ethyl)-N-hydroxyurea, prepared as described in U.S. Pat. No. 5,185,363, for N-1-(fur-3-yl)ethyl-N-hydroxyurea. $^1$H NMR (300 MHz, DMSO-$d_6$, mixture of diastereomers) δ 1.39 (d, 3H, J=8 Hz), 1.55 (bm, 3H), 1.82 (bm, 3H), 3.90 and 3.93 (s, 3H), 4.90 and 4.98 (bs, 2H), 5.69 (bm, 1H), 6.68 (bm, 2H), 7.01 (bm, 1H), 7.09–7.21 (m, 2H), 7.28–7.43 (m, 6H), 7.53–7.77 (m, 3H). MS (DCI/NH$_3$) m/e 498 (M+H)$^+$. Analysis calc'd for $C_{31}H_{31}NO_5$: C, 74.83; H, 6.28; N, 2.82. Found: C, 74.35; H, 6.44; N, 2.94.

EXAMPLE 18

Preparation of
N-[(S)-2-(6-methoxynaphth-2-yl)propionyloxy]-
N-[3-(5-(4-fluorophenoxy)fur-
2-yl)-1-methyl-2-propynyl]urea

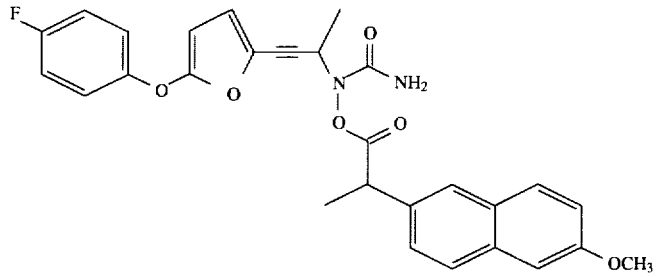

Step 1: 5-(4-fluorophenoxy)-2-furfuraldehyde

To a stirred suspension of pentane washed 80% sodium hydride (53 g, 177 mmol) in THF (200 mL) under argon was added p-fluorophenol (19.9 g, 177 mmol) in small portions as a solid. After gas evolution ceased, the THF was removed in vacuo. The crude phenoxide was redissolved in DMF (200 mL) and cooled to 0° C. To the stirred mixture was added 5-nitro furfuraldehyde (25 g, 177 mmol) as a DMF (50 mL) solution via dropping funnel. During the addition the reaction mixture became very thick, requiring the addition of additional DMF (150 mL), removal from the ice bath and swirling. The addition was then completed with stirring in the ice bath. The reaction mixture was stirred for 0.5 hours and poured into ice water. The mixture was extracted with ether (200 mL×8), the ether layers combined washed with 10% NaOH (3×100 mL), and water (3×100 mL), dried over $MgSO_4$, filtered, and concentrated in vacuo. The resulting solid was dissolved in ethyl acetate, treated with decolorizing carbon, filtered and concentrated in vacuo. Recrystallization of the solid from ether/hexane afforded 25 g (68%) of 5-(4-fluorophenoxy)-2-furfuraldehyde as a slightly yellow solid.

Step 2: 2-[5-(4-fluorophenoxy)-2-furyl]-1,1-dibromoethene

A mixture of carbon tetrabromide (100.73 g, 303 mmol), zinc dust (19.84 g, 303 mmol) and triphenylphosphine (79.56 g, 303 mmol) in $CH_2Cl_2$ (700 mL) was stirred overnight under an argon atmosphere. A $CH_2Cl_2$(100 mL) solution of 5-(4-fluorophenoxy)- 2-furfuraldehyde (25 g, 121 mmol), prepared as in step 1, was added to the resulting suspension and stirring was continued for 2 hours at room temperature. The reaction mixture was diluted with pentane (1600 mL) and after further stirring the pentane/$CH_2Cl_2$ was decanted. The pentane/$CH_2Cl_2$ solution was flitered through a short column of silica gel topped with celite. The filtrate was concentrated to afford 43 g (98%) of 2-[5-(4-fluorophenoxy)-2-furyl]-1,1-dibromoethene as a yellow oil.

Step 3: 2-[5-(4-fluorophenoxy)-2-furyl]-ethyne

To a stirred −78° C. solution in THF (200 mL) under argon of 2-[5-(4-fluorophenoxy)- 2-furyl]-1,1-dibromoethene (23.1 g, 63.81 mmol), prepared as in step 2, was added n-butyl lithium (51.0 mL, 127.62 mmol, 2.5M in hexanes). The reaction was stirred for 0.5 hours at −78° C. Aqueous ammonium chloride was added to the cold reaction, the ice bath was removed and the reaction mixture allowed to warm to room temperature. The majority of THF was removed in vacuo. The resulting mixture was partitioned between water and ether. The combined ether layers were dried over $MgSO_4$, filtered, and concentrated in vacuo. The residue was purified by chromatography on silica gel (hexanes) to give 6.5 g (50%) of 2-[5-(4-fluorophenoxy)- 2-furyl]-ethyne.

Step 4: 4-[5-(4-fluorophenoxy)-2-furyl]-3-butyne-2-ol

Lithium diisopropylamide was generated by the addition of n-butyl lithium (14.2 mL, 35,4 mmol, 2.5M in hexanes) to a stirred −78° C. THF (100 mL) solution as of diisopropylamine (3.58 g, 35.4 mmol) followed by warming to −5° C. (ice/methanol) and stirring for 0.5 hours. To this stirred solution was added the 2-[5-(4-fluorophenoxy)- 2-furyl]-ethyne (6.5 g, 32.2 mmol) prepared in step 3 as a THF solution via syringe. The reaction was stirred 0.5 hours and acetaldehyde (3.11 g, 70.8 mmol) was added via syringe, the ice bath was removed, and the reaction warmed to room temperature. Water was added and most of the THF removed in vacuo. The resulting mixture was partitioned between water and ethyl acetate. The combined ethyl acetate layers were dried over $MgSO_4$, filtered, and concentrated in vacuo. The residue was purified by chromatography on silica gel (30% ether/hexanes) to give 6.39 g (73%) of 4-[5-(4-fluorophenoxy)-2-furyl]-3-butyne-2-ol as a slightly yellow solid. mp(ether/hexanes) 56°–57.5° C. $^1$H NMR (300 MHz, $CDCl_3$) δ 1.54 (d, 3H, J=7 Hz), 1.88 (d, 1H, J=6 Hz), 4.75 (m, 1H), 5.47 (d, 1H, J=4 Hz), 6.53 (d, 1H, J=4 Hz), 7.04 (m, 4H). MS (DCI/$NH_3$) m/e 247 $(M+H)^+$, 229.

Step, 5: N,O-bis(carbophenoxy)-N-{4-[5-(4-fluorophenoxy)-2-furyl]-3-butyn-2-yl}hydroxylamine To a 0° C. stirred THF solution (100 mL) of 4-[5-(4-fluorophenoxy)-2-furyl]- 3-butyne-2-ol (6.39 g, 25.98 mmol, 1.0 eq) prepared in step 4, bis N,O-carbophenoxyhydroxylamine (7.80 g, 28.57 mmol, 1.1 eq) and triphenylphosphine (8.17 g, 31.17 mmol, 1.2 eq) was added a THF solution (25 ml) of diisopropylazodicarboxylate (6.30 g, 31.17 mmol, 1.2 eq) via dropping funnel. The reaction mixture was stirred for 0.5 hours at room temperature and concentrated in vacuo. The crude reaction mixture was dissolved in a minimum of $CH_2Cl_2$, loaded onto a silica gel column and eluted with $CH_2Cl_2$. Fractions containing the desired compound were combined and concentrated in vacuo. The residue was purified by chromatography on silica gel (50% $CH_2Cl_2$/hexanes) to afford 7.7 g (53%) of N,O-bis(carbophenoxy)-N-{ 4-[5-(4-fluorophenoxy)-2-furyl]-3-butyn-2-yl}hydroxylamine as a thick yellow oil.

Step 6: N-{3-[5-(4-fluorophenoxy)fur-2-yl]-1-methyl-2-propynyl}-N-hydroxyurea

In a screw top vessel with a teflon O-ring was placed the N,O-bis(carbophenoxy)-N-{ 4-[5-(4-fluorophenoxy)-2-furyl]-3-butyn-2-yl}hydroxylamine (7.50 g, 14.97 mmol) prepared in step 5. Liquid ammonia (~10–15 mL) was condensed using a cold finger (dry ice/acetone) into the cooled (also −78° C.) reaction vessel. The vessel was sealed, the ice bath was removed, and the reaction was stirred overnight at room temperature. The vessel was then recooled to −78° C. and opened, the ice bath was removed and the reaction mixture allowed to come to room temperature and evaporate the ammonia. The crude residue was dissolved in ~15% MeOH/CH₂Cl₂ and passed through a short silica column. Fractions containing product were combined, concentrated in vacuo and triturated (to remove phenol) with 1:1 ether:hexane (2x) to give 2.6 g of N-{3-[5-(4-fluorophenylmethyloxy)fur-2-yl]- 1-methyl-2-propynyl}-N-hydroxyurea as a yellow solid. Recrystalization from ethyl acetate/hexanes gave 2.3 g of the title compound as an off white solid. The mother liquor and the ether/hexane washes from the phenol trituration were combined, concentrated and purified by chromatography on silica gel (5% MeOH/CH₂Cl₂). Recrystallization of the resulting solid gave an additional 0.3 g of the title compound. Total yield 2.6 g (57%). mp 148°–150° C. (dec). ¹H NMR (300 MHz, DMSO-d6) δ 1.34 (d, 3H, J=7 Hz), 5.13 (q, 1H, J=7 Hz), 5.76 (d, 1H, J=3 Hz), 6.56 (bs, 2H), 6.74 (d, 1H, J=3 Hz), 7.13–7.30 (m, 4H), 9.37 (s, 1H). MS (DCI/NH₃) m/e 305 (M+H)⁺, 289, 229. Anal. Calcd. for C₁₅H₁₃FN₂O₄: C, 59.21; H, 4.31; N, 9.21. Found: C, 59.09; H,4.32; N, 9.15.

Step 7: N-[(S)-2-(6-methoxynaphth-2-yl)propionyloxy]-N-[3-(5-(4-fluorophenoxy)fur- 2-yl-1-methyl-2-propyl]urea The desired material was prepared according to the procedure of Example 1, except substituting N-{3-[5-(4-fluorophenylmethyloxy)fur-2-yl]-1-methyl-2-propynyl }-N-hydroxyurea, prepared as in step 6, for N-1-(fur-3-yl)ethyl-N-hydroxyurea. ¹H NMR (300 MHz, DMSO-d₆, mixture of diastereomers) δ 0.72 and 1.06 (bm, 3H), 1.55 (m, 3H), 3.85 (s, 3H), 4.22 (m, 1H), 5.11 and 5.22 (m, 1H), 5.74 and 5.77 (d, 1H, J=3.5 Hz), 6.61 (m, 1H), 6.93 and 7.06 (bs, 2H), 7.08 and 7.12 (t, 1H, J=2.5 Hz), 7.17–7.32 (m, 5H), 7.45 (m, 1H), 7.67–7.81 (m, 3H). MS (DCI/NH₃) m/e 517 (M+H)⁺. Analysis calc'd for C₂₉H₂₅FN₂O₆.0.75 H₂O: C, 65.71; H, 5.04; N, 5.29. Found: C, 65.73; H, 4.90; N, 5.23.

EXAMPLE 19

Preparation of
N-[2-(4-(2-methylpropyl)phenyl)propionyloxy]-
N-[3-(5-(4-fluorophenoxy)fur-
2-yl)-1-methyl-2-propynyl]urea

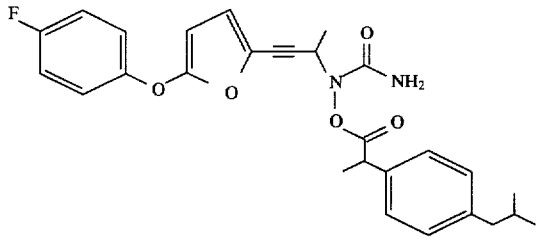

The desired material was prepared, as an oil, according to the procedure of Example 18, except substituting ibuprofen for naproxen. ¹H NMR (300 MHz, DMSO-d₆, mixture of diastereomers) δ 0.79 (m, 6H), 1.02 and 1.45 (m, 6H), 2.36 (bd, 2H, J=6.5 Hz), 1.74 (m, 1H), 4.03 (m, 1H), 5.11 and 5.21 (m, 1H), 5.81 (m, 1H), 6.73 (m, 1H), 6.90 and 7.00 (bs, 2H), 7.04 (m, 2H), 7.23 (m, 6H). MS (DCI/NH₃) m/e 493 (M+H)⁺. Analysis calc'd for C₂₈H₂₉FN₂O₅: C, 67.66; H, 5.99; N, 5.64. Found: C, 67.45; H, 5.95; N, 5.55.

EXAMPLE 20

Preparation of
N-[2-(4-(2-methylpropyl)phenyl)propionyloxy]-
N-[1-(fur-3-yl)ethyl]urea

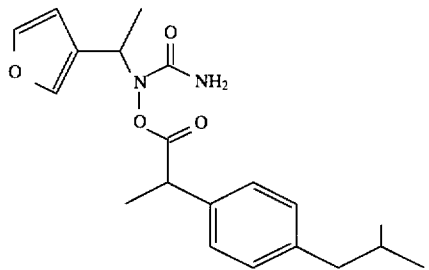

The desired material was prepared according to the procedure of Example 1, except substituting ibuprofen for naproxen. m.p. 55°–59° C. ¹H NMR (300 MHz, DMSO-d₆, mixture of diastereomers) δ 0.77 and 1.13 (bm, 3H), 0.85 (m, 6H), 1.39 (bm, 3H), 1.81 (m, 1H), 2.43 and 2.45 (d, 3H, J=7 Hz), 3.97 (m, 1H), 5.17 (q, 1H, J=7 Hz), 5.90 and 6.14 (bs, 2H), 6.74 (bs, 1H), 7.06 (bm, 2H), 7.11–7.25 (bm, 3H), 7.45 (bs, 1H). MS (DCI/NH₃) m/e 359 (M+H)⁺. Analysis calc'd for C₂₀H₂₆N₂O₄: C, 67.01; H, 7.31; N, 7.82. Found: C, 67.02; H, 7.28; N, 7.87.

EXAMPLE 21

Preparation of
N-[(S)-2-(6-methoxynaphth-2-yl)propionyloxy]-
N-[3-(5-( 4-fluorophenylmethyl)thien-2-
yl)-(R)-1-methyl-2-propynyl]urea

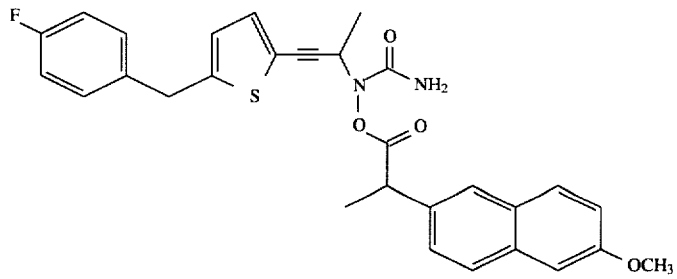

To a stirred dry methylene chloride (150 mL) solution of N-3-[5-(4-fluorophenylmethyl)thien- 2-yl]-1-methyl-2-propynyl-N-hydroxyurea (2.0 g, 6.6 mmole), prepared as described in U.S. Pat. No. 5,288,751, was added naproxen (1.82 g, 7.92 mmole) and dicyclohexylcarbodimide (DCC) (1.64 g, 7.92 mmole). The mixture was stirred for 3 hours at ambient temperature and concentrated in vacuo. The residue diluted with ether, filtered and washed with additional ether. The ether layer was washed with water and dried over $MgSO_4$. The ether solution was concentrated in vacuo and the residue was purified by chromatography on silica gel (50% ethyl acetate/hexanes) to yield 2.6 g (74%) of N-[(S)-2-(6-methoxynaphth-2-yl)propionyloxy] -N-[3-(5-(4-fluorophenylmethyl)thien-2-yl)-(R)-1-methyl-2-propynyl]urea as a thick clear oil that on prolonged exposure to high vacuum gave a white brittle foam. $[\alpha]_D^{25°}$ –70.3° (c=1.7, $CH_2Cl_2$). $^1H$ NMR (300 MHz, DMSO-d-6) δ 0.75 (bm, 3H), 1.54 (d, 3H, J=7.5 Hz), 3.86 (s, 3H), 4.13 (s, 2H), 4.20 (q, 1H, J=7 Hz), 5.09 (bm, 1H), 6.81 (d, 1H, J=4 Hz), 6.92 (m, 1H), 7.03 (bs, 2H), 7.08–7.22 (m, 3H), 7.26–7.36 (m, 3H), 7.44 (m, 1H), 7.70–7.80 (m, 3H). MS ($DCI/NH_3$) m/e 548 $(M+NH_4)^+$, 531 $(M+H)^+$, 301, 258, 243. Analysis calcd for $C_{30}H_{27}FN_2O_4S$: C, 67.90; H, 5.12; N, 5.27. Found: C, 67.85; H, 5.00; N, 5.27.

EXAMPLE 22

Preparation of
N-[2-(4-benzyloxy-3-chlorophenyl)acetyloxyl]-
(R)-N-[3-(5-( 4-fluorophenylmethyl)thien-2-yl)-
1-methyl-2-propynyl]urea The desired compound is prepared according to the method of Example 21, except substituting butibufen for naproxen.

EXAMPLE 23

Preparation of
N-[2-(4-(2-methylpropyl)phenyl)butyryloxy]-
N-[3-(5-(4-fluorophenylmethyl)thien-
2-yl)-(R)-1-methyl-2-propynyl]urea The desired compound is prepared according to the method of Example 21, except substituting benzofenac for naproxen.

EXAMPLE 24

Preparation of
N-[2-(fluoren-2-yl)propionyloxy]-N-[3-(5-
(4-fluorophenylmethyl)thien-
2-yl)-(R)-1-methyl-2-propynyl]urea The desired compound is prepared according to the method of Example 21, except substituting cycloprofen for naproxen.

EXAMPLE 25

Preparation of
N-[2-(N-cinnamoyl-5-methoxy-2-methyl-
[1H]-indol-3-yl)acetoxy]-N-[
3-(5-(4-fluorophenylmethyl)thien-2-
yl)-(R)-1-methyl-2-propynyl]urea The desired compound is prepared according to the method of Example 21, except substituting cinmetacin for naproxen.

EXAMPLE 26

Preparation of
N-[(5-chloro-6-phenylindan-2-yl)carbonyloxy]-
N-[3-(5-( 4-fluorophenylmethyl)thien-
2-yl)-(R)-1-methyl-2-propynyl]urea The desired compound is prepared according to the method of Example 21, except substituting clidinac for naproxen.

EXAMPLE 27

Preparation of
N-[2-(2-(2,4-dichlorophenoxy)phenyl)acetoxy]-
N-[3-(5-( 4-fluorophenylmethyl)thien-2-yl)-
(R)-1-methyl-2-propynyl]urea The desired compound is prepared according to the method of Example 21, except substituting fenclofenac for naproxen.

EXAMPLE 28

Preparation of
N-[2-(3-phenoxyphenyl)propionyloxy]-N-[3-
(5-(4-fluorophenylmethyl)thien-
2-yl)-(R)-1-methyl-2-propynyl]urea The desired compound is prepared according to the method of Example 21, except substituting fenoprofen for naproxen.

EXAMPLE 29

Preparation of
N-[2-(3-phenylbenzo[b]fur-7-yl)propionyloxy]-
N-[3-(5-( 4-fluorophenylmethyl)thien-2-yl)-
(R)-1-methyl-2-propynyl]urea The desired compound is prepared according to the method of Example 21, except substituting furaprofen for naproxen.

EXAMPLE 30

Preparation of
N-[2-(2,3-dihydro-2-ethylbenzo[b]fur-
5-yl)propionyloxy]-N-[3-(5-(
4-fluorophenylmethyl)thien-2-
yl)-(R)-1-methyl-2-propynyl]urea The desired compound is prepared according to the method of Example 21, except substituting furofenac for naproxen.

EXAMPLE 31

Preparation of
N-[2-(4(2-methylpropyl)phenyl)acetyloxy]-
N-[3-5-( 4-fluorophenylmethyl)thien-2-
yl)-(R)-1-methyl-2-propynyl]urea The desired compound is prepared according to the method of Example 21, except substituting ibufenac for naproxen.

EXAMPLE 32

Preparation of
N-[2-(4-(2,3-dihydro-1-oxoisoindolyl)
phenyl)propionyloxy]-N-[
3-(5-(4-fluorophenylmethyl)thien-2-yl)-
1-methyl-2-propynyl]urea The desired compound is prepared according to the method of Example 2, except substituting indoprofen for naproxin.

EXAMPLE 33

Preparation of
N-[2-(5-fluoro-2-methyl-1((4-methylsuflinyl)
phenyl)methylene)-(
1H)indene-3-acetyloxy]-N-[3-(5-(4-
fluorophenylmethyl)thien-2-yl)-1-
methyl-2-propynyl]urea The desired compound is prepared according to the method of Example 2, except substituting sulindac for naproxin.

EXAMPLE 34

Preparation of
N-[2-(6-methoxynaphth-2-yl)acetyloxy]-
N-[3-(5-(4-fluorophenylmethyl)thien-
2-yl)-(R)-1-methyl-2-propynyl]urea

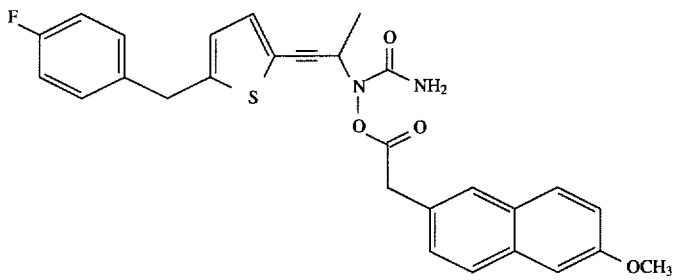

Step 1: 6-methoxynaphthyl-2-carhoxaldehyde

To a −78° C. solution in THF (150 mL) of 2-Bromo-6-methoxynaphthalene (5 g, 21.1 mmol) was slowly added nBuLi (8.5 ml, 2.5M in hexanes). The reaction mixture was stirred at −78° C. for ½ hour and was quenched with DMF (3 ml). The reaction mixture was stirred overnight at ambient temperature, H$_2$O (10 ml) was added, and the organic layer was separated, dried over MgSO$_4$, filtered, and concentrated in vacuo. The residue was putified by chromatography on silica gel, (15% ethylacetate in pentane) to provide 3.6 g (92% yield) of 6-methoxynaphthyl-2-carboxaldehyde. $^1$HNMR (300 MHz, CDCl$_3$) δ 10.1 (1H, s), 8.25 (s, 1H), 7.78– 7.84 (m, 3H) 7.17–7.26 (m, 2H), 3.97 (s, 3H). MS (DCI/NH$_3$) m/e 187 (M+H)$^+$, 204 (M+NH$_4$)$^+$.

Step 2: 6-methoxynaphthyl-2-acetonitrile

A solution of tosylmethyl isocyanide (2.83 g, 14.5 mmol) in 1,2-dimethoxyethane was added dropwise to a stirred −30° C. suspension under N$_2$ of t-BuOK (3.2 g, 28.9 mmol) in 30 ml of dimethoxyethane. The reaction mixture was cooled to −60° C. and a solution of 6-methoxynaphthyl-2-carboxaldehyde (2.69 g, 14.47 mmol), prepared as in step 1, in dimethoxyethane (25 mL) was added dropwise. After 1.5 hours, methanol (35 ml) was added to the cold solution and the reaction mixture was warmed to reflux and heated for 15 min. After removal of the solvent in vacuo, the residue was taken up in a mixture of water (48 ml) and acetic acid (2 ml) and extracted with methylene chloride (3×50 ml). The organic extracts were combined and washed with aqueous saturated NaHCO$_3$, dried over MgSO$_4$, filtered, and concentrated in vacuo. Purification be chromatography on silica gel, (1:1, methylene chloride/pentane) afforded 1.43 g (50%) of 6-methoxynaphthyl-2-acetonitrile. $^1$H NMR (300 MHz, CDCl$_3$) δ 7.72–7.76 (m, 3H), 7.12–7.38 (m, 3H), 3.94 (s, 3H) 3.88 (s, 3H). MS (DCI/NH$_3$) m/e 197(M)$^+$, 215 (M+NH$_4$)$^+$.

Step 3: 6-methoxynaphth-2-ylacetic acid

A suspension in sodium hydroxide (20% aqueous solution) of 6-methoxynaphthyl- 2-acetonitrile (4.00 g, 20.3 mmol), prepared as in step 2, was refluxed for 24 hours. The reaction mixture was cooled in an ice bath, acidified with 50% hydrochloric acid, and extracted with ethyl acetate. The organic layer was washed with brine, dried over MgSO$_4$, filtered, and concentrated in vacuo. Crystallization from ethyl acetate/pentane afforded 3.8 g (87%) 6-methoxynaphth-2-ylacetic acid. mp 173°–74° C. $^1$H NMR (300 MHz, CDCl$_3$) δ 10.15 (br s, 1H), 7.65– 7.72 (m, 3H), 7.12–7.38 (m, 3H), 3.92 (s, 3H), 3.78 (s, 3H). MS (DCI/NH$_3$) m/e 234 (M+H)$^+$.

Step 4: N-[2-(6-methoxynaphth-2-yl)acetyloxyl-N-[3-(5-(4-fluorophenylmethyl)thien- 2-yl)-(R)-1-methyl-2-propynyl] urea To a solution in methylene chloride (15 mL) of 6-methoxynaphth-2-ylacetic acid (87.5 mg, 4.05 mmol), prepared as in step 3, was added oxalyl choride (0.5 ml, 4.0 mmol) and the reaction mixture was refluxed for 2 hours. The solvents were removed in vacuo and the residue was taken up in dry methylene chloride. A 0° C. solution in methylene chloride (10 mL) of (R)-N-3-[5-(4-fluorophenylmethyl)thien-2-yl] -1-methyl-2-propynyl-N-hydroxyurea (954 mg, 3 mmol), prepared as described in U.S. Pat. No. 5,288,751, and triethylamine (0.45 ml, 3.1 mmol) was added slowly, and the reaction mixture was stirred for 2 hours. The solvents were removed in vacuo and the residue was purified by chromatography on silica gel (10% ethyl acetate/methylene chloride) to provide 1.1 g (72% yield) of N-[2-(6-methoxynaphth- 2-yl)acetyloxy]-N-[3-(5-(4-fluorophenylmethyl)thien-2-yl)-(R)-1-methyl-2-propynyl] urea. $^1$H NMR (300 MHz, CDCl$_3$) δ 7.62–7.72 (m, 3H), 7.4 (dd, 1H, J= 9, 1.5 Hz), 6.95–7.25 (m, 7H), 6.62 (d, 1H, J=4 Hz), 5.36 (q, 1H, J=7 Hz), 4.72 (s, 2H), 4.05 (s, 2H), 3.93 (s, 3H), 1.4 (d, 3H, J=7 Hz). MS (DCI/NH$_3$) m/e 517(M+H)$^+$. Analysis calculated for C$_{29}$H$_{25}$FN$_2$O$_4$S; C, 67.42; H, 4.87; N, 5.42. Found C, 67.20; H, 4.69; N, 5.36.

EXAMPLE 35

Preparation of
N-[2-(6-methoxynaphth-2-yl)acetyloxy]-N-
[1-(benzo[b]thien-2-yl)ethyl]urea

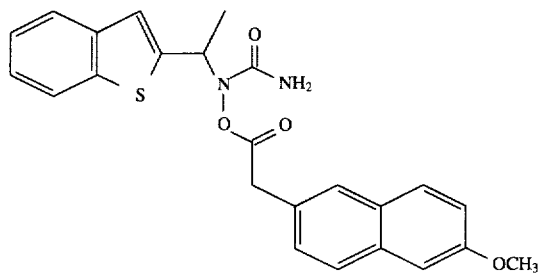

The desired compound was prepared according to the method of Example 34, except substituting N-1-(benzo[b]thien-2-yl)ethyl-N-hydroxyurea, prepared as described in U.S. Pat. No. 4,873,259, for N-3-[5-(4-fluorophenylmethyl)thien-2-yl]- 1-methyl-2-propynyl-N-hydroxyurea. The desired product was obtained in 63.6% yield. $^1$H NMR (300 MHz, CDCl$_3$) d7.58–7.8 (5H, m), 7.29–7.35 (3H, m), 7.05–7.2 (3H, m), 5.85 (1H, q, J=6 Hz), 4.64 (2H, Br s), 3.92 (3H, s), 3.82 (2H, s), 1.55 (3H, d, J=6 Hz); MS m/e 452 (M+NH4); Analysis calculated for $C_{24}H_{22}N_2O_4S._{1/3}H_2O$; C, 65.43; H, 5.03; N, 6.35; Found C, 65.53; H, 5.04; N, 6.34

EXAMPLE 36

Preparation of N-[(-2-acetoxybenzoyl)oxy]-N-[1-(benzo[b]thien-2-yl)ethyl]urea

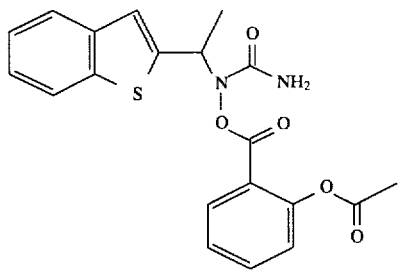

The desired material was prepared according to the procedure of Example 3, except substituting acetylsalicylic acid for ibuprofen. mp 141°–143° C. $^1$H NMR (300 MHz, DMSO-d$_6$) δ 1.55 (bm, 3H), 2.16 and 2.22 (s, 3H), 5.79 (bm, 1H), 6.91 (bm, 2H), 7.25–7.50 (m, 5H), 7.68–7.82 (m, 2H), 7.95 (m, 2H). MS (DCI/NH$_3$) m/e 399 (M+H)$^+$. Analysis calc'd for $C_{20}H_{18}N_2O_5S$: C, 60.29; H, 4.55; N, 7.03. Found: C, 60.74; H, 4.72; N, 6.57.

EXAMPLE 37

Preparation of
N-[2-(acetoxybenzoyl)oxy]-N-[3-(5-(4-fluorophenoxy)fur-2-yl)-1-methyl- 2-propynyl]urea

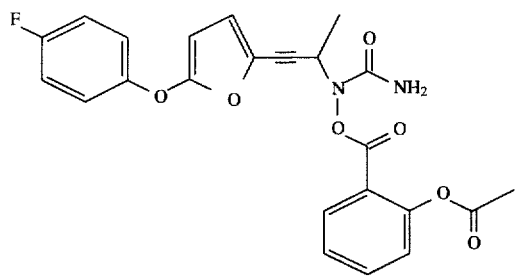

The desired material was prepared according to the procedure of Example 18, except substituting acetylsalicylic acid for naproxen. $^1$H NMR (300 MHz, DMSO-d$_6$) δ 1.36 (bm, 3H), 2.26 (s, 3H), 5.34 (bm, 1H), 5.74 (m, 1H), 6.73 (bm, 1H), 7.02 (bs, 2H), 7.15–7.33 (m, 5H), 7.43 (m, 1H), 7.73 (m, 1H), 8.04 (m, 1H). MS (DCI/NH$_3$) m/e 467 (M+H)$^+$.

EXAMPLE 38

Preparation of (R)-N-[2-(6-methoxynaphth-2-yl) propionyloxy]-N-[1-(benzo[b]thien-2-yl)ethyl]-N'-methylurea The desired compound is prepared according to the method of Example 2, except substituting N-1-(benzo[b]thien-2-yl)ethyl-N-hydroxy-N' methyl urea, prepared as described in U.S. Pat. No. 4,873,259. for N-1-(benzo[b]thien-2-yl)ethyl-N-hydroxyurea.

EXAMPLE 39

Preparation of
N-[(S)-2-(6-methoxynaphth-2-yl)propionyloxy]-N-[3-(5-( 4-fluorophenylmethyl)thien-2-yl)-(R)-1-methyl-2-propynyl]-N'-methylurea The desired compound is prepared according to the method of Example 21, except substituting (R)-N-3-[5-(4-fluorophenylmethyl)thien-2-yl]-1-methyl-2-propynyl-N-hydroxy-N'-methylurea for (R)-N-3-[5-(4-fluorophenylmethyl)thien-2-yl]- 1-methyl-2-propynyl-N-hydroxyurea.

EXAMPLE 40

Preparation of
N-[2-(2-(2,4-dichlorophenylamino)phenyl) acetyloxy]-N-[3-(5-( 4-fluorophenylmethyl)thien-2-yl)-(R)-1-methyl-2-propynylurea The desired compound is prepared according to the method of Example 21, except substituting diclofenac for naproxen.

EXAMPLE 41

Preparation of
N-[(2-(2,6-dichloro-3-methylphenylamino)
benzoyl)oxy]-N-[3-(5-(
4-fluorophenylmethyl)thien-2-yl)-(R)-
1-methyl-2-propynyl]urea The desired compound is prepared according to the method of Example 21, except substituting meclofenamic acid for naproxen.

EXAMPLE 42

Preparation of
N-[(2-(2,6-dichloro-3-methylphenylamino)
benzoyl)oxy]-N-[1-(benzo[b]thien- 2-yl)ethyl]urea The desired compound is prepared according to the method of Example 2, except substituting meclofenamic acid for naproxen.

We claim
1. A compound or pharmaceutically acceptable salt thereof of formula

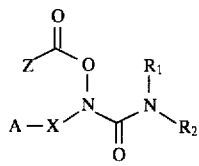

wherein
A is selected from the group consisting of
  (a) unsubstituted carbocyclic aryl
  (b) carbocyclic aryl substituted with
    alkyl of one to six carbon atoms,
    haloalkyl of one to six carbon atoms,
    hydroxyalkyl of one to six carbon atoms,
    alkoxy of one to twelve carbon atoms,
    alkoxyalkoxyl in which the two alkoxy portions are independently of one to six carbon atoms,
    alkylthio of one to six carbon atoms,
    hydroxy,
    halogen,
    cyano,
    amino,
    alkylamino of one to six carbon atoms,
    dialkylamino in which the two alkyl groups are independently of one to six carbon atoms,
    alkanoylamino of from two to eight carbon atoms,
    N-alkanoyl-N-alkylamino in which the alkanoyl is of two to eight carbon atoms and the alkyl group is of one to six carbon atoms,
    alkylaminocarbonyl of two to eight carbon atoms,
    dialkylaminocarbonyl in which the two alkyl groups are independently of one to six carbon atoms,
    carboxyl,
    alkoxycarbonyl of two to eight carbon atoms,
    unsubstituted phenyl,
    phenyl, substituted with
      alkyl of one to six carbon atoms,
      haloalkyl of one to six carbon atoms,
      alkoxy of one to six carbon atoms,
      hydroxy or
      halogen,
    unsubstituted phenoxy,
    phenoxy, substituted with
      alkyl of one to six carbon atoms,
      haloalkyl of one to six carbon atoms,
      alkoxy of one to six carbon atoms,
      hydroxy or
      halogen,
    unsubstituted phenylthio,
    phenylthio, substituted with
      alkyl of one to six carbon atoms,
      haloalkyl of one to six carbon atoms,
      alkoxy of one to six carbon atoms,
      hydroxy or
      halogen,
    unsubstituted phenylalkyl wherein the alkyl portion is of one to twelve carbon atoms,
    phenylalkyl wherein the alkyl portion is of one to twelve carbon atoms and the phenyl moiety is substituted with alkyl of one to six carbon atoms,
      haloalkyl of one to six carbon atoms,
      alkoxy of one to six carbon atoms,
      hydroxy or
      halogen,
    unsubstituted pyridyl,
    pyridyl, substituted with
      alkyl of one to six carbon atoms,
      haloalkyl of one to six carbon atoms,
      alkoxy of one to six carbon atoms,
      hydroxy or
      halogen,
    unsubstituted pyridyloxy,
    pyridyloxy, substituted with alkyl of one to six carbon atoms,
      haloalkyl of one to six carbon atoms,
      alkoxy of one to six carbon atoms,
      hydroxy or
      halogen,
    unsubstituted pyridylalkyl wherein the alkyl portion is of one to twelve carbon atoms,
    pyridylalkyl wherein the alkyl portion is of one to twelve carbon atoms and the pryidyl portion is substituted with
      alkyl of one to six carbon atoms,
      haloalkyl of one to six carbon atoms,
      alkoxy of one to six carbon atoms,
      hydroxy or
      halogen;
  (c) unsubstituted furyl,
  (d) furyl substituted with
    alkyl of one to six carbon atoms,
    haloalkyl of one to six carbon atoms,
    halogen,
    unsubstituted phenyl,
    phenyl, substituted with
      alkyl of one to six carbon atoms,
      haloalkyl of one to six carbon atoms,
      alkoxy of one to six carbon atoms,
      hydroxy or
      halogen,
    unsubstituted phenoxy,
    phenoxy, substituted with
      alkyl of one to six carbon atoms,
      haloalkyl of one to six carbon atoms,
      alkoxy of one to six carbon atoms,
      hydroxy or
      halogen,
    unsubstituted phenylthio,
    phenylthio, substituted with alkyl of one to six carbon atoms,
haloalkyl of one to six carbon atoms,
alkoxy of one to six carbon atoms,
hydroxy or
halogen,
unsubstituted phenylalkyl wherein the alkyl portion is of one to twelve carbon atoms,
phenylalkyl wherein the alkyl portion is of one to twelve carbon atoms and the phenyl moiety is substituted with
alkyl of one to six carbon atoms,
haloalkyl of one to six carbon atoms,
alkoxy of one to six carbon atoms,
hydroxy or
halogen,
unsubstituted pyridyl,
pyridyl, substituted with
alkyl of one to six carbon atoms,
haloalkyl of one to six carbon atoms,
alkoxy of one to six carbon atoms,
hydroxy or
halogen,
unsubstituted pyridyloxy,
pyridyloxy, substituted with
alkyl of one to six carbon atoms,
haloalkyl of one to six carbon atoms,
alkoxy of one to six carbon atoms,
hydroxy or
halogen,
unsubstituted pyridylalkyl wherein the alkyl portion is of one to twelve carbon atoms,
pyridylalkyl wherein the alkyl portion is of one to twelve carbon atoms and the pryidyl portion is substituted with
alkyl of one to six carbon atoms,
haloalkyl of one to six carbon atoms,
alkoxy of one to six carbon atoms,
hydroxy or
halogen;
(e) unsubstituted benzo[b]furyl,
(f) benzo[b]furyl substituted with
alkyl of one to six carbon atoms,
haloalkyl of one to six carbon atoms;
alkoxyl of one to six carbon atoms,
hydroxy, or
halogen;
(g) unsubstituted thienyl,
(h) thienyl substituted with
alkyl of one to six carbon atoms,
unsubstituted phenyl,
phenyl, substituted with
alkyl of one to six carbon atoms,
haloalkyl of one to six carbon atoms,
alkoxy of one to six carbon atoms,
hydroxy or
halogen,
unsubstituted phenoxy,
phenoxy, substituted with
alkyl of one to six carbon atoms,
haloalkyl of one to six carbon atoms,
alkoxy of one to six carbon atoms,
hydroxy or
halogen,
unsubstituted phenylthio,
phenylthio, substituted with
alkyl of one to six carbon atoms,
haloalkyl of one to six carbon atoms,
alkoxy of one to six carbon atoms,
hydroxy or
halogen,
unsubstituted phenylalkyl wherein the alkyl portion is of one to twelve carbon atoms,
phenylalkyl wherein the alkyl portion is of one to twelve carbon atoms and the phenyl moiety is substituted with
alkyl of one to six carbon atoms,
haloalkyl of one to six carbon atoms,
alkoxy of one to six carbon atoms,
hydroxy or
halogen,
unsubstituted pyridyl,
pyridyl, substituted with
alkyl of one to six carbon atoms,
haloalkyl of one to six carbon atoms,
alkoxy of one to six carbon atoms,
hydroxy or
halogen,
unsubstituted pyridyloxy,
pyridyloxy, substituted with
alkyl of one to six carbon atoms,
haloalkyl of one to six carbon atoms,
alkoxy of one to six carbon atoms,
hydroxy or
halogen,
unsubstituted pyridylalkyl wherein the alkyl portion is of one to twelve carbon atoms,
pyridylalkyl wherein the alkyl portion is of one to twelve carbon atoms and the pryidyl portion is substituted with
alkyl of one to six carbon atoms,
haloalkyl of one to six carbon atoms,
alkoxy of one to six carbon atoms,
hydroxy or
halogen;
(i) unsubstituted benzo[b]thienyl,
(j) benzo[b]thienyl substituted with
alkyl of one to six carbon atoms,
haloalkyl of one to six carbon atoms;
alkoxyl of one to six carbon atoms,
hydroxy, or
halogen;
(k) unsubstituted pyridyl,
(l) pyridyl substituted with
alkyl of one to six carbon atoms,
haloalkyl of one to six carbon atoms;
alkoxyl of one to six carbon atoms,
hydroxy,
halogen,
unsubstituted phenylalkyl wherein the alkyl portion is of one to twelve carbon atoms,
phenylalkyl wherein the alkyl portion is of one to twelve carbon atoms and the phenyl moiety is substituted with
alkyl of one to six carbon atoms,
haloalkyl of one to six carbon atoms,
alkoxy of one to six carbon atoms,
hydroxy or
halogen,
(m) unsubstituted quinolyl,
(n) quinolyl substituted with
alkyl of one to six carbon atoms,
haloalkyl of one to six carbon atoms;
alkoxyl of one to six carbon atoms,
hydroxy, or halogen, and
(o) unsubstituted indolyl,
(p) indolyl substituted with
  alkyl of one to six carbon atoms,
  haloalkyl of one to six carbon atoms;
  alkoxyl of one to six carbon atoms,
  hydroxy, or
  halogen;
X is selected from the group consisting of
  unsubstituted alkyl of one to six carbon atoms,
  alkyl of one to six carbon atoms substituted with
    hydroxy,
    halogen,
    cyano,
    alkoxy of one to six carbon atoms,
    carboxy,
    alkoxycarbonyl of one to six carbon atoms, or
    aminocarbonyl,
  unsubstituted alkenyl of two to six carbon atoms,
  alkenyl of two to six carbon atoms substituted with
    hydroxy,
    halogen,
    cyano,
    alkoxy of one to six carbon atoms,
    carboxy,
    alkoxycarbonyl of one to six carbon atoms, or
    aminocarbonyl,
  unsubstituted alkynyl of two to six carbon atoms, and
  alkynyl of two to six carbon atoms substituted with
    hydroxy,
    halogen,
    cyano,
    alkoxy of one to six carbon atoms,
    carboxy,
    alkoxycarbonyl of one to six carbon atoms, or
    aminocarbonyl,
$R^1$ and $R^2$ are independently selected from the group
  consisting of
  hydrogen,
  hydroxy, and
  alkyl of one to six carbon atoms,
  provided that $R^1$ and $R^2$ are not both hydroxyl;
Z is a residue of a non-steroidal anti-inflammatory drug of
  the general formula Z—COOH, said non-steroidal anti-
  inflammatory drug selected from the group consisting
  of
  acetylsalicylic acid,
  benoxaprofen,
  benzofenac,
  bucloxic acid,
  butibufen,
  carprofen,
  cicloprofen,
  cinmetacin,
  clidanac,
  clopirac,
  diclofenac,
  etodolac,
  fenbufen,
  fenclofenac,
  fenclorac,
  fenoprofen,
  fentiazac,
  flunoxaprofen,
  flurbiprofen,
  furaprofen,
  furobufen,
  furofenac,
  ibuprofen,
  ibufenac,
  indomethacin,
  indoprofen,
  isoxepac,
  ketoprofen,
  ketorolac,
  lonazolac,
  meclofenamic acid,
  6-methoxynaphth-2-ylacetic acid (4-MNA),
  metiazinic acid,
  miroprofen,
  naproxen,
  oxaprozin,
  oxepinac,
  pirprofen,
  pirazolac,
  protizinic acid,
  sulindac,
  suprofen,
  tiaprofenic acid,
  tolmetin, and
  zomepirac.

2. A compound or pharmaceutically acceptable salt thereof as defined by claim 1 wherein Z is a residue of a non-steroidal anti-inflammatory drug of the general formula Z—COOH, said non-steroidal anti-inflammatory drug selected from the group consisting of
  acetylsalicylic acid
  benzofenac,
  bucloxic acid,
  butibufen,
  cicloprofen,
  cinmetacin,
  clidanac,
  diclofenac,
  fenbufen,
  fenclofenac,
  fenoprofen,
  ibuprofen,
  ibufenac,
  indomethacin,
  ketoprofen,
  meclofenamic acid,
  6-methoxynaphth-2-ylacetic, acid (4-MNA),
  naproxen, and
  sulindac.

3. A compound as defined by claim 1 or pharmaceutically acceptable salt thereof wherein
A is selected from the group consisting of
  (a) unsubstituted carbocyclic aryl, and
  (b) carbocyclic aryl substituted with
    alkyl of one to six carbon atoms,
    haloalkyl of one to six carbon atoms,
    hydroxyalkyl of one to six carbon atoms,
    alkoxy of one to twelve carbon atoms,
    alkoxyalkoxyl in which the two alkoxy portions may
      each independently contain one to six carbon
      atoms,
    alkylthio of one to six carbon atoms,
    hydroxy,
    halogen,
    cyano,
    amino,
    alkylamino of one to six carbon atoms,
    dialkylamino in which the two alkyl groups may
      independently contain one to six carbon atoms, alkanoylamino of from two to eight carbon atoms,
N-alkanoyl-N-alkylamino in which the alkanoyl may contain two to eight carbon atoms and the alkyl groups may contain one to six carbon atoms,
alkylaminocarbonyl of two to eight carbon atoms,
dialkylaminocarbonyl in which the two alkyl groups may independently contain one to six carbon atoms,
carboxyl,
alkoxycarbonyl of two to eight carbon atoms,
unsubstituted phenyl,
phenyl, substituted with
   alkyl of one to six carbon atoms,
   haloalkyl of one to six carbon atoms,
   alkoxy of one to six carbon atoms,
   hydroxy or
   halogen,
unsubstituted phenoxy,
phenoxy, substituted with
   alkyl of one to six carbon atoms,
   haloalkyl of one to six carbon atoms,
   alkoxy of one to six carbon atoms,
   hydroxy or
   halogen,
unsubstituted phenylthio,
phenylthio, substituted with
   alkyl of one to six carbon atoms,
   haloalkyl of one to six carbon atoms,
   alkoxy of one to six carbon atoms,
   hydroxy or
   halogen,
unsubstituted phenylalkyl wherein the alkyl portion is of one to twelve carbon atoms,
phenylalkyl wherein the alkyl portion is of one to twelve carbon atoms and the phenyl moiety is substituted with
   alkyl of one to six carbon atoms,
   haloalkyl of one to six carbon atoms,
   alkoxy of one to six carbon atoms,
   hydroxy or
   halogen,
unsubstituted pyridyl,
pyridyl, substituted with
   alkyl of one to six carbon atoms,
   haloalkyl of one to six carbon atoms,
   alkoxy of one to six carbon atoms,
   hydroxy or
   halogen,
unsubstituted pyridyloxy,
pyridyloxy, substituted with
   alkyl of one to six carbon atoms,
   haloalkyl of one to six carbon atoms,
   alkoxy of one to six carbon atoms,
   hydroxy or
   halogen,
unsubstituted pyridylalkyl wherein the alkyl portion is of one to twelve carbon atoms,
pyridylalkyl wherein the alkyl portion is of one to twelve carbon atoms and the pryidyl portion is substituted with
   alkyl of one to six carbon atoms,
   haloalkyl of one to six carbon atoms,
   alkoxy of one to six carbon atoms,
   hydroxy or
   halogen.

4. A compound or pharmaceutically acceptable salt thereof as defined by claim 2 wherein A is selected from the group consisting of (a) unsubstituted furyl,
(b) furyl substituted with
   alkyl of one to six carbon atoms,
   haloalkyl of one to six carbon atoms,
   halogen,
   unsubstituted phenyl,
   phenyl, substituted with
      alkyl of one to six carbon atoms,
      haloalkyl of one to six carbon atoms,
      alkoxy of one to six carbon atoms,
      hydroxy or
      halogen,
   unsubstituted phenoxy,
   phenoxy, substituted with
      alkyl of one to six carbon atoms,
      haloalkyl of one to six carbon atoms,
      alkoxy of one to six carbon atoms,
      hydroxy or
      halogen,
   unsubstituted phenylthio,
   phenylthio, substituted with
      alkyl of one to six carbon atoms,
   haloalkyl of one to six carbon atoms,
      alkoxy of one to six carbon atoms,
      hydroxy or
      halogen,
   unsubstituted phenylalkyl wherein the alkyl portion is of one to twelve carbon atoms,
   phenylalkyl wherein the alkyl portion is of one to twelve carbon atoms and the phenyl moiety is substituted with
      alkyl of one to six carbon atoms,
      haloalkyl of one to six carbon atoms,
      alkoxy of one to six carbon atoms,
      hydroxy or
      halogen,
   unsubstituted pyridyl,
   pyridyl, substituted with
      alkyl of one to six carbon atoms,
      haloalkyl of one to six carbon atoms,
      alkoxy of one to six carbon atoms,
      hydroxy or
      halogen,
   unsubstituted pyridyloxy,
   pyridyloxy, substituted with
      alkyl of one to six carbon atoms,
      haloalkyl of one to six carbon atoms,
      alkoxy of one to six carbon atoms,
      hydroxy or
      halogen,
   unsubstituted pyridylalkyl wherein the alkyl portion is of one to twelve carbon atoms,
   pyridylalkyl wherein the alkyl portion is of one to twelve carbon atoms and the pryidyl portion is substituted with alkyl of one to six carbon atoms,
   haloalkyl of one to six carbon atoms,
   alkoxy of one to six carbon atoms,
   hydroxy or
   halogen,
(c) unsubstituted thienyl,
(d) thienyl substituted with
   alkyl of one to six carbon atoms,
   unsubstituted phenyl,
   phenyl, substituted with
      alkyl of one to six carbon atoms,
      haloalkyl of one to six carbon atoms,
      alkoxy of one to six carbon atoms, hydroxy or
halogen,
unsubstituted phenoxy,
phenoxy, substituted with
    alkyl of one to six carbon atoms,
    haloalkyl of one to six carbon atoms,
    alkoxy of one to six carbon atoms,
    hydroxy or
    halogen,
unsubstituted phenylthio,
phenylthio, substituted with
    alkyl of one to six carbon atoms,
    haloalkyl of one to six carbon atoms,
    alkoxy of one to six carbon atoms,
    hydroxy or
    halogen,
unsubstituted phenylalkyl wherein the alkyl portion is of one to twelve carbon atoms,
phenylalkyl wherein the alkyl portion is of one to twelve carbon atoms and the phenyl moiety is substituted with alkyl of one to six carbon atoms,
    haloalkyl of one to six carbon atoms,
    alkoxy of one to six carbon atoms,
    hydroxy or
    halogen,
unsubstituted pyridyl,
pyridyl, substituted with
    alkyl of one to six carbon atoms,
    haloalkyl of one to six carbon atoms,
    alkoxy of one to six carbon atoms,
    hydroxy or
    halogen,
unsubstituted pyridyloxy,
pyridyloxy, substituted with
    alkyl of one to six carbon atoms,
    haloalkyl of one to six carbon atoms,
    alkoxy of one to six carbon-atoms,
    hydroxy or
    halogen,
unsubstituted pyridylalkyl wherein the alkyl portion is of one to twelve carbon atoms,
pyridylalkyl wherein the alkyl portion is of one to twelve carbon atoms and the pryidyl portion is substituted with alkyl of one to six carbon atoms,
    haloalkyl of one to six carbon atoms,
    alkoxy of one to six carbon atoms,
    hydroxy or
    halogen,
(e) unsubstituted pyridyl, and
(f) pyridyl substituted with
    alkyl of one to six carbon atoms,
    haloalkyl of one to six carbon atoms;
    alkoxyl of one to six carbon atoms,
    hydroxy,
    halogen,
unsubstituted phenylalkyl wherein the alkyl portion is of one to twelve carbon atoms,
phenylalkyl wherein the alkyl portion is of one to twelve carbon atoms and the phenyl moiety is substituted with alkyl of one to six carbon atoms,
haloalkyl of one to six carbon atoms,
alkoxy of one to six carbon atoms,
hydroxy or
halogen.

5. A compound or pharmaceutically acceptable salt thereof as defined by claim 2 wherein A is selected from
(a) unsubstituted benzo[b]thienyl,
(b) benzo[b]thienyl substituted with
    alkyl of one to six carbon atoms,
    haloalkyl of one to six carbon atoms;
    alkoxyl of one to six carbon atoms,
    hydroxy, or
    halogen.

6. A compound or pharmaceutically acceptable salt thereof as defined by claim 1 selected from the group consisting of N-[(S)-2-(6-methoxynaphth-2-yl)propionyloxy]-N-[1-(fur-3-yl)ethyl]urea, N-[(S)-2-(6-methoxynaphth-2-yl)propionyloxy]-N-[1-(benzo[b]thien-2-yl)ethyl]urea, N-[2-(4-(2-methylpropyl)phenyl)propionyloxy]-N-[1-(benzo[b]thien-2-yl)ethyl] urea, N-[2-(N-(4-chlorobenzoyl)-5-methoxy-2-methyl-[1H]-indol-3-yl)acetoxy]-N-[ 1-(benzo[b]thien-2-yl)ethyl] urea, N-[(S)-2-(6-methoxynaphth-2-yl)propionyloxy]-N-[1-(4-phenylmethyloxyphenyl)ethyl]urea, N-[(S)-2-(6-methoxynaphth-2-yl)propionyloxy]-N-[3-(5-(4-fluorophenoxy)fur- 2-yl)-1-methyl-2-propynyl]urea N-[2-(4-(2-methylpropyl)phenyl)propionyloxy]-N-[3-(5-(4-fluorophenoxy)fur- 2-yl)-1-methyl-2-propynyl]urea, N-[2-(4-(2-methylpropyl)phenyl)propionyloxy-]N-[1-(fur-3-yl)ethyl]urea, N-[(S)-2-(6-methoxynaphth-2-yl)propionyloxy]-N-[3-(5-(4-fluorophenylmethyl)thien- 2-yl)-(R)-1-methyl-2-propynyl]urea, N-[2-(6-methoxynaphth-2-yl)acetyloxy]-N-[3-(5-(4-fluorophenylmethyl)thien- 2-yl)-(R)-1-methyl-2-propynyl] urea, N-[2-(6-methoxynaphth-2-yl)acetyloxy]-N-[1-(benzo[b]thien-2-yl)ethyl]urea, N-[(-2-acetoxybenzoyl)oxy]-N-[1-(benzo[b]thien-2-yl)ethyl]urea, and N-[2-(acetoxybenzoyl)oxy]-N-[3-(5-( 4-fluorophenoxy)fur-2-yl)-1-methyl-2-propynyl]urea.

7. A composition for inhibiting cyclooxygenase or 5-lipoxygenase activity comprising a pharmaceutical carrier and a therapeutically effective amount of a compound as defined in claim 1.

8. A method for inhibiting cyclooxygenase or 5-lipoxygenase activity in a mammal in need of such treatment comprising administering to the mammal a therapeutically effective amount of a compound as defined in claim 1.

\* \* \* \* \*

UNITED STATES PATENT AND TRADEMARK OFFICE
CERTIFICATE OF CORRECTION

PATENT NO. : 5,516,789
DATED : May, 14, 1996
INVENTOR(S) : C.D.W. Brooks, et. Al.

It is certified that error appears in the above-indentified patent and that said Letters Patent is hereby corrected as shown below:

Column 41, line 37, change "carbon-atoms" to --carbon atoms--.

Signed and Sealed this

Tenth Day of December, 1996

*Attest:*

BRUCE LEHMAN

*Attesting Officer*    *Commissioner of Patents and Trademarks*